US012778869B2

(12) United States Patent
Sinha et al.

(10) Patent No.: US 12,778,869 B2
(45) Date of Patent: Nov. 3, 2026

(54) CLEANSING COMPOSITIONS COMPRISING DIVALENT SALTS

(71) Applicant: L'OREAL, Paris (FR)

(72) Inventors: Ritesh Kumar Sinha, Linden, NJ (US); Hungta Lin, Teaneck, NJ (US); Trung Vu, Clark, NJ (US); Hy Si Bui, Piscataway, NJ (US); Mariko Hasebe, New York, NY (US)

(73) Assignee: L'OREAL, Paris (FR)

( * ) Notice: Subject to any disclaimer, the term of this patent is extended or adjusted under 35 U.S.C. 154(b) by 660 days.

(21) Appl. No.: 18/344,204

(22) Filed: Jun. 29, 2023

(65) Prior Publication Data

US 2025/0009628 A1 Jan. 9, 2025

(51) Int. Cl.

| | |
|---|---|
| ***A61K 8/00*** | (2006.01) |
| ***A61K 8/02*** | (2006.01) |
| ***A61K 8/44*** | (2006.01) |
| ***A61K 8/46*** | (2006.01) |
| ***A61Q 19/10*** | (2006.01) |

(52) U.S. Cl.

CPC ............ *A61K 8/466* (2013.01); *A61K 8/0295* (2013.01); *A61K 8/44* (2013.01); *A61Q 19/10* (2013.01); *A61K 2800/596* (2013.01)

(58) Field of Classification Search

None

See application file for complete search history.

(56) References Cited

U.S. PATENT DOCUMENTS

| | | | |
|---|---|---|---|
| 7,744,655 | B2 | 6/2010 | De Boni et al. |
| 9,248,083 | B2 | 2/2016 | Aires et al. |
| 9,408,785 | B2 | 8/2016 | Pistorio et al. |
| 10,328,009 | B1 | 6/2019 | Elsen-Wahrer et al. |
| 10,548,832 | B2 | 2/2020 | Thomas et al. |
| 10,561,592 | B2 | 2/2020 | Darras et al. |
| 10,912,728 | B2 | 2/2021 | D'Arras et al. |
| 11,458,084 | B2 | 10/2022 | Park et al. |
| 2002/0176843 | A1 | 11/2002 | Creton |
| 2002/0182238 | A1 | 12/2002 | Creton |
| 2005/0158269 | A1 | 7/2005 | Simonet |
| 2007/0128256 | A1 | 6/2007 | Aubrun-Sonneville |
| 2008/0014162 | A1 | 1/2008 | Willemin et al. |
| 2011/0171151 | A1 | 7/2011 | Arnaud et al. |
| 2013/0011360 | A1 | 1/2013 | Viravau et al. |
| 2013/0210696 | A1 | 8/2013 | Vethamuthu et al. |
| 2014/0017184 | A1 | 1/2014 | Fumagalli et al. |
| 2015/0297481 | A1 | 10/2015 | Wahler et al. |
| 2015/0359722 | A1 | 12/2015 | Thomas et al. |
| 2017/0189286 | A1 | 7/2017 | George et al. |
| 2017/0326044 | A1 | 11/2017 | Springinsfeld et al. |
| 2019/0060196 | A1 | 2/2019 | Elsen et al. |
| 2019/0216692 | A1 | 7/2019 | Luan et al. |
| 2019/0290557 | A1 | 9/2019 | Shimizu et al. |
| 2019/0365611 | A1* | 12/2019 | Brown ..................... A61K 8/42 |
| 2020/0188282 | A1 | 6/2020 | Chodorowski-Kimmes |
| 2020/0188283 | A1 | 6/2020 | Chodorowski-Kimmes |
| 2022/0362128 | A1 | 11/2022 | Hamazaki et al. |
| 2022/0378683 | A1 | 12/2022 | Stebbins et al. |

FOREIGN PATENT DOCUMENTS

| | | | |
|---|---|---|---|
| CN | 104739673 | A | 7/2015 |
| CN | 109172493 | A | 1/2019 |
| CN | 112494342 | A | 3/2021 |

OTHER PUBLICATIONS

Preliminary Search Report and Written Opinion issued on Apr. 9, 2024 for corresponding French Application No. FR 2309818.

Database GNPD [Online]; Mintel; Anonymous: "Shampoo" 2022 XP093144844.

Database GNPD [Online]; Mintel; Anonymous: "Softening Body Wash" 2015 XP093144849.

* cited by examiner

*Primary Examiner* — Necholus Ogden, Jr.

(74) *Attorney, Agent, or Firm* — POLSINELLI PC

(57) ABSTRACT

The present disclosure is drawn to cleansing compositions. The cleansing compositions include: (a) one or more anionic surfactants; (b) one or more nonionic emulsifiers having a Hydrophile-Lipophile Balance (HLB) of about 6 or less; (c) one or more salts providing divalent cations having a charge density of about 40 to about 200 $C/mm^3$ and a water solubility of at least 400 g/L; (d) one or more anionic polymers; (e) one or more water soluble solvents; and (f) water. The cleansing compositions have a unique lamellar liquid crystal structure and are useful in methods for cleansing the body, including the skin and hair.

16 Claims, No Drawings

CLEANSING COMPOSITIONS COMPRISING DIVALENT SALTS

FIELD OF THE DISCLOSURE

The present disclosure relates to cleansing compositions and methods for cleansing the hair or body with the compositions.

BACKGROUND

Most "dirt" contains traces of oil and grease, which stick to the surface of the skin and hair. Rinsing with only water is not sufficient to adequately remove the oil and grease. The main functional ingredients in cleansing compositions are surfactants. Surfactants interact with water, thereby allowing it to "wet" surfaces more efficiently. The surfactant-water combination is then able to surround the specks of dirt and carry them away with rinsing. Agitation of the water solution, for example by rubbing hands together during washing or lathering shampoo into hair, also aids the process of removing dirt.

Conventional cleansing compositions such as shampoos, for example, contain surfactants in various amounts. Anionic surfactants are typically included because they provide foaming to a composition. Nonionic surfactants may also be included to provide cleansing, solubilizing, and dispersing properties but are usually less irritating than anionic surfactants. Nonionic surfactants, however, often exhibit less foaming ability and do not provide any enhancement to viscosity (e.g., often a composition is thinner and runnier with increased amounts of nonionic surfactants). In some cleansing applications, higher viscosity is desired for the product's handling or ease of application. In addition, higher viscosity personal care products are more aesthetically appealing to many consumers.

The development of cleansing compositions has been driven by a need for certain performance properties that consumers find desirable. For example, consumers seek cleansing compositions that foam and cleanse well, have a certain "thickness" (viscosity), and are mild to the skin and hair. The cleansing compositions should also rinse away from the body with ease. However, the addition of a particular component to a cleansing composition often will enhance one desired property to the detriment of another desired property. It is therefore difficult to achieve a perfect balance of desirable performance properties.

SUMMARY OF THE DISCLOSURE

The present disclosure is drawn to cleansing compositions containing a unique combination of divalent salts, nonionic emulsifiers having a low Hydrophile-Lipophile Balance (HLB), and non-hydrophobically modified anionic polymers. The inventors discovered that divalent cations in combination with non-hydrophobically modified anionic polymers imparts viscosity, stability, and hydrating properties to cleansing composition that include anionic surfactants. The cleansing compositions have a unique microstructure, resulting in pleasant creamy texture, which is surprisingly stable. During use, the compositions provide a high degree of foam, are gentle, and leave the skin and hair hydrated. The cleansing composition typically includes:

(a) one or more anionic surfactants;

(b) one or more nonionic emulsifiers having a Hydrophile-Lipophile Balance (HLB) of about 6 or less;

(c) one or more salts providing divalent cations having a charge density of about 40 to about 200 C/mm$^3$ and a water solubility of at least 400 g/L;

(d) one or more anionic polymers; and (e) one or more water soluble solvents; and (f) water;

wherein all percentages are based on a total weight of the composition.

Nonlimiting examples of sulfate surfactants include alkyl sulfates and alkyl ether sulfates. Nonlimiting examples of alkyl sulfates include sodium lauryl sulfate (SLS), sodium dodecyl sulfate (SDS), or a combination thereof. A nonlimiting examples of an alkyl ether sulfate includes sodium lauryl ether sulfate (SLES).

Nonlimiting examples of non-sulfate anionic surfactants include acyl isethionates, acyl amino acids (such as acyl taurates, acyl glycinates, acyl glutamates, and acyl sarcosinates), alkyl sulfonates, alkyl sulfosuccinates, alkyl sulfoacetates, alkoxylated monoacids, salts thereof, and a combination thereof. In a preferred embodiment, at least one of the one or more non-sulfate anionic surfactants is an alkyl sulfonate. Nonlimiting examples of alkyl sulfonates include $C_8$-$C_{16}$ alkyl benzene sulfonates, $C_1$-$C_{20}$ paraffin sulfonates, $C_{10}$-$C_{24}$ olefin sulfonates, salts thereof, and combinations thereof. $C_{10}$-$C_{24}$ olefin sulfonates are particularly preferred. A non-limiting but particularly useful example of a $C_{10}$-$C_{24}$ olefin sulfonate that can be used in the instant compositions is sodium $C_{14}$-$C_{16}$ olefin sulfonate, or a combination thereof.

The cleansing composition includes one or more nonionic emulsifiers having a Hydrophile-Lipophile Balance (HLB) of about 6 or less. Nonlimiting examples include sorbitan esters, glyceryl esters, polyglyceryl esters, glycol esters, sucrose esters, methyl glucose esters, ethoxylated methyl glucose esters, or a combination thereof. Nonlimiting examples of glycol esters include glycol distearate, glycol hydroxystearate, glycol oleate, glycol ricinoleate, glycol stearate, propylene glycol isostearate, propylene glycol hydroxystearate, propylene glycol laurate, propylene glycol myristate, propylene glycol oleate, propylene glycol ricinoleate, propylene glycol stearate, and combinations thereof.

The cleansing composition includes one or more salts providing divalent cations having a charge density of about 40 to about 200 C/mm$^3$ and a water solubility of at least 500 g/L. Nonlimiting examples of salts that provide divalent cations include magnesium and calcium salts such as magnesium chloride, calcium chloride, magnesium sulfate, magnesium thiosulfate, calcium thiosulfate, magnesium pyrrolidone carboxylate (magnesium pidolate), calcium pyrrolidone carboxylate (calcium pidolate), magnesium gluconate, or a combination thereof Nonlimiting examples of anionic polymers include polyacrylic acid, polymethacrylic acid, carboxyvinylpolymer, an acrylate copolymer, a sulfonate polymer, a carboxymethylcellulose, a carboxy guar gum, a copolymer of ethylene and maleic acid, an acrylate silicone polymer, and a combination thereof. Particularly useful anionic polymers include copolymers of two or more monomers selected from acrylic acid, methacrylic acid, vinyl monomers, and (meth)acrylamide.

The cleansing composition typically includes substantial amounts of one or more water-soluble solvents (or "water-soluble organic solvents"). Nonlimiting examples of water-soluble solvents include glycerin, $C_2$-$C_6$ mono-alcohols, polyols (polyhydric alcohols), glycols, and a combination thereof.

In various embodiments, the cleansing composition includes one or more additional components. For example, the cleansing composition may include one or more skin active agents, one or more miscellaneous ingredients, or a combination thereof.

The cleansing compositions are particularly useful for cleansing the body including skin and hair. The compositions exhibit good cleansing ability, lather, foaming and foam stability, and hydrating properties. Additionally, the cleansing compositions are particularly well-suited for cleansing artificially colored hair because the compositions preserve the color of the artificially colored hair while simultaneously providing shine, smoothness, moisturization, and a pleasant tactile film to hair.

DETAILED DESCRIPTION OF THE DISCLOSURE

The instant disclosure is drawn to cleansing compositions. The cleansing compositions clean the body and impart shine, hydration, and a pleasant tactile feel to skin and hair. Furthermore, the cleansing compositions have a sufficient and desirable rheology due to a unique interaction between salts providing divalent cations and anionic polymers. The inventors surprisingly discovered an association between the divalent cations and anionic polymers provides thickening to the compositions resulting in the composition having an unusual and unique lamellar liquid crystal structure. The cleansing composition typically includes:

(a) about 5 to about 25 wt. % of one or more anionic surfactants;

(b) about 1 to about 10 wt. % of one or more nonionic emulsifiers having a Hydrophile-Lipophile Balance (HLB) of about 6 or less;

(c) about 0.05 to about 5 wt. % of one or more salts providing divalent cations having a charge density of about 40 to about 200 $C/mm^3$ and a water solubility of at least 400 g/L;

(d) about 0.5 to about 6 wt. % of one or more anionic polymers; and (e) about 5 to about 55 wt. % of one or more water soluble solvents; and (f) about 25 to about 75 wt. % of water;

wherein all percentages by weight are based on a total weight of the compositions.

The cleansing composition typically has a lamellar liquid crystal structure with an opaque or white appearance, in the form of a cream of paste. Further, the composition is typically an oil-in-water emulsion or dispersion.

Due to the robust cleansing and hydrating properties of the cleansing compositions, the cleansing composition is useful as a skin cleanser, a hair cleanser (shampoo), a body wash, a cleansing and hydrating cleanser, an all-in-one conditioning and shampooing composition, or a general-purpose cleanser.

The cleansing compositions are particularly useful in methods for cleansing the body, including the skin and hair. Such methods include applying the cleansing composition to the body or area to be cleansed (skin or hair), massaging the cleansing composition over the area to be cleans (or throughout the hair), and rinsing the cleansing composition from the body.

(a) Anionic Surfactants

Useful anionic surfactants include, but are not limited to, sulfate surfactants, acyl isethionates, acyl amino acids (such as acyl taurates, acyl glycinates, acyl glutamates, and acyl sarcosinates), alkyl sulfonates, alkyl sulfosuccinates, alkyl sulfoacetates, alkoxylated monoacids, salts thereof, and a combination thereof.

The total amount of anionic surfactants in the cleansing compositions will vary. Nonetheless, in certain embodiments, the cleansing composition includes 5 to about 30 wt. % of the one or more anionic surfactants, based on the total weight of the cleansing composition. In further embodiments, the cleansing composition includes about 5 to about 25 wt. %, about 5 to about 20 wt. %, about 5 to about 18 wt. %, about 5 to about 15 wt. %, about 5 to about 12 wt. %, about 5 to about 10 wt. %, about 8 to about 30 wt. %, about 8 to about 25 wt. %, about 8 to about 20 wt. %, about 8 to about 18 wt. %, about 8 to about 15 wt. %, about 8 to about 12 wt. %, about 10 to about 30 wt. %, about 10 to about 25 wt. %, about 10 to about 20 wt. %, about 10 to about 18 wt. %, or about 12 to about 18 wt. % of the one or more sulfate surfactants, based on the total weight of the cleansing composition.

The one or more anionic surfactants can include one or more sulfate surfactants, one of more non-sulfate surfactants, or a combination thereof. Nonlimiting examples of sulfate surfactants include alkyl sulfates and alkyl ether sulfates. Useful alkyl sulfates include, but are not limited to, $C_{8-18}$ alky sulfates, more preferably $C_{12-18}$ alkyl sulfates, preferably in the form of a salt with a solubilizing cation such as sodium, potassium, ammonium or substituted ammonium. Nonlimiting examples include sodium lauryl sulfate (SLS), sodium dodecyl sulfate (SDS), or a combination thereof. Useful alkyl ether sulfates include, but are not limited to, those having the formula: $RO(CH_2CH_2O)_nSO_3M$; wherein R is an alkyl or alkenyl having from 8 to 18 (preferably 12 to 18) carbon atoms; n is a number having an average value of greater than at least 0.5, preferably between 1 and 3, more preferably between 2 and 3; and M is a solubilizing cation such as sodium, potassium, ammonium or substituted ammonium. An example is sodium lauryl ether sulfate (SLES).

Nonlimiting examples of non-sulfate surfactants include acyl amino acids, alkyl sulfonates, alkyl sulfosuccinates, acyl isethionates, alkyl sulfoacetates, alkoxylated monoacids, salts thereof, and a combination thereof are provided below (i) Acyl Amino Acids Acyl amino acids that may be used include, but are not limited to, amino acid surfactants based on alanine, arginine, aspartic acid, glutamic acid, glycine, isoleucine, leucine, lysine, phenylalanine, serine, tyrosine, valine, sarcosine, threonine, and taurine. The most common cation associated with the acyl amino acid can be sodium or potassium. Alternatively, the cation can be an organic salt such as triethanolamine (TEA) or a metal salt. Non-limiting examples of useful acyl amino acids include those of formula (I):

(I)

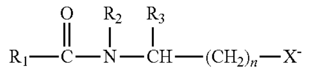

wherein R, $R^1$, $R^2$ and $R^3$ are each independently selected from H or an alkyl chain having 1-24 carbon atoms, said chain being saturated or unsaturated, linear or branched, and X is $COO^-$ or $SO_3^-$.

(i-a) Acyl Sarcosinates

Nonlimiting examples of acyl sarcosinates include those of Formula (II) or salt thereof:

$$RCON(CH_3)CH_2COOX \quad (II)$$

wherein R is C8 to C22 alkyl or alkenyl, X is hydrogen, alkali metal, ammonium, C1 to C6 alkylamine or amino alcohol.

More specific but nonlimiting examples of acyl sarcosinates include potassium lauroyl sarcosinate, potassium cocoyl sarcosinate, sodium cocoyl sarcosinate, sodium lauroyl sarcosinate, sodium myristoyl sarcosinate, sodium oleoyl sarcosinate, sodium palmitoyl sarcosinate, and ammonium lauroyl sarcosinate. In some instances, sodium lauroyl sarcosinate is preferred.

The total amount of the one or more acyl sarcosinates in the cleansing composition, if present, will vary. Nonetheless, in certain embodiments, the cleansing composition includes about 0.1 to about 18 wt. % of the one or more acyl sarcosinates, based on the total weight of the cleansing composition. In further embodiments, the cleansing composition includes about 0.1 to about 15 wt. %, about 0.1 to about 12 wt. %, about 0.1 to about 10 wt. %, about 0.1 to about 8 wt. %, about 0.1 to about 5 wt. %, about 0.1 to about 3 wt. %, about 1 to about 18 wt. %, about 1 to about 15 wt. %, about 1 to about 12 wt. %, about 1 to about 10 wt. %, about 1 to about 8 wt. %, about 1 to about 5 wt. %, about 2 to about 18 wt. %, about 2 to about 15 wt. %, about 2 to about 12 wt. %, about 2 to about 10 wt. %, about 2 to about 8 wt. %, about 2 to about 5 wt. %, about 5 to about 18 wt. %, about 5 to about 15 wt. %, about 5 to about 12 wt. %, about 5 to about 12 wt. %. about 5 to about 10 wt. %, about 10 to about 18 wt. %, or about 10 to about 15 wt. % of the one or more acyl sarcosinates, based on the total weight of the cleansing composition. In further embodiments, the cleansing composition includes about 0.1 to about 5 wt. %, about 3 to about 8 wt. %, about 5 to about 10 wt. %, about 8 to about 12 wt. %, or about 10 to about 18 wt. % of the one or more acyl sarcosinates, based on the total weight of the cleansing composition.

(i-b) Acyl Taurates

Non-limiting examples of acyl taurates include those of formula (III):

(III)

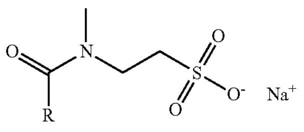

wherein R, $R^1$, $R^2$ and $R^3$ are each independently selected from H or an alkyl chain having 1-24 carbon atoms, or from 6-20 carbon atoms, or from 8 to 16 carbon atoms, said chain being saturated or unsaturated, linear or branched, and X is $COO^-$ or $SO_3^-$. Non-limiting examples of acyl taurate salts include sodium cocoyl taurate and sodium methyl cocoyl taurate.

The total amount of the one or more acyl taurates in the cleansing composition, if present, will vary. Nonetheless, in certain embodiments, the cleansing composition includes about 0.1 to about 18 wt. % of the one or more acyl taurates, based on the total weight of the cleansing composition. In further embodiments, the cleansing composition includes about 0.1 to about 15 wt. %, about 0.1 to about 12 wt. %, about 0.1 to about 10 wt. %, about 0.1 to about 8 wt. %, about 0.1 to about 5 wt. %, about 0.1 to about 3 wt. %, about 1 to about 18 wt. %, about 1 to about 15 wt. %, about 1 to about 12 wt. %, about 1 to about 10 wt. %, about 1 to about 8 wt. %, about 1 to about 5 wt. %, about 2 to about 18 wt. %, about 2 to about 15 wt. %, about 2 to about 12 wt. %, about 2 to about 10 wt. %, about 2 to about 8 wt. %, about 2 to about 5 wt. %, about 5 to about 18 wt. %, about 5 to about 15 wt. %, about 5 to about 12 wt. %, about 5 to about 12 wt. %. about 5 to about 10 wt. %, about 10 to about 18 wt. %, or about 10 to about 15 wt. % of the one or more acyl taurates, based on the total weight of the cleansing composition. In further embodiments, the cleansing composition includes about 0.1 to about 5 wt. %, about 3 to about 8 wt. %, about 5 to about 10 wt. %, about 8 to about 12 wt. %, or about 10 to about 18 wt. % of the one or more acyl taurates, based on the total weight of the cleansing composition.

(i-c) Acyl Glycinates

Non-limiting examples of useful acyl glycinates include those of formula (IV):

(IV)

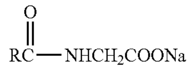

wherein R is an alkyl chain of 8 to 16 carbon atoms. Sodium is shown as the cation in the above formula (IV) but the cation may be an alkali metal ion such as sodium or potassium, ammonium ions, or alkanolammonium ions such as monoethanolammonium or triethanolammonium ions. Non-limiting examples of acyl glycinates include sodium cocoyl glycinate, sodium lauroyl glycinate, sodium myristoyl glycinate, potassium lauroyl glycinate, and potassium cocoyl glycinate, and in particular sodium cocoyl glycinate.

The total amount of the one or more acyl glycinates in the cleansing composition, if present, will vary. Nonetheless, in certain embodiments, the cleansing composition includes about 0.1 to about 18 wt. % of the one or more acyl glycinates, based on the total weight of the cleansing composition. In further embodiments, the cleansing composition includes about 0.1 to about 15 wt. %, about 0.1 to about 12 wt. %, about 0.1 to about 10 wt. %, about 0.1 to about 8 wt. %, about 0.1 to about 5 wt. %, about 0.1 to about 3 wt. %, about 1 to about 18 wt. %, about 1 to about 15 wt. %, about 1 to about 12 wt. %, about 1 to about 10 wt. %, about 1 to about 8 wt. %, about 1 to about 5 wt. %, about 2 to about 18 wt. %, about 2 to about 15 wt. %, about 2 to about 12 wt. %, about 2 to about 10 wt. %, about 2 to about 8 wt. %, about 2 to about 5 wt. %, about 5 to about 18 wt. %, about 5 to about 15 wt. %, about 5 to about 12 wt. %, about 5 to about 12 wt. %. about 5 to about 10 wt. %, about 10 to about 18 wt. %, or about 10 to about 15 wt. % of the one or more acyl glycinates, based on the total weight of the cleansing composition. In further embodiments, the cleansing composition includes about 0.1 to about 5 wt. %, about 3 to about 8 wt. %, about 5 to about 10 wt. %, about 8 to about 12 wt. %, or about 10 to about 18 wt. % of the one or more acyl glycinates, based on the total weight of the cleansing composition.

(i-d) Acyl Glutamates

Non-limiting examples of useful acyl glutamates include those of formula (V):

(V)

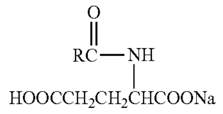

wherein R is an alkyl chain of 8 to 16 carbon atoms. Sodium is shown as the cation in the above formula (XI) but the cation may be an alkali metal ion such as sodium or potassium, ammonium ions, or alkanolammonium ions such as monoethanolammonium or triethanolammonium ions. Non-limiting examples of acyl glutamates include dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, triethanolamine mono-cocoyl glutamate, triethanolamine lauroylglutamate, and disodium cocoyl glutamate. In some cases, sodium stearoyl glutamate is particularly preferred.

The total amount of the one or more acyl glutamates in the cleansing composition, if present, will vary. Nonetheless, in certain embodiments, the cleansing composition includes about 0.1 to about 18 wt. % of the one or more acyl glutamates, based on a total weight of the cleansing composition. In further embodiments, the cleansing composition includes about 0.1 to about 15 wt. %, about 0.1 to about 12 wt. %, about 0.1 to about 10 wt. %, about 0.1 to about 8 wt. %, about 0.1 to about 5 wt. %, about 0.1 to about 3 wt. %, about 1 to about 18 wt. %, about 1 to about 15 wt. %, about 1 to about 12 wt. %, about 1 to about 10 wt. %, about 1 to about 8 wt. %, about 1 to about 5 wt. %, about 2 to about 18 wt. %, about 2 to about 15 wt. %, about 2 to about 12 wt. %, about 2 to about 10 wt. %, about 2 to about 8 wt. %, about 2 to about 5 wt. %, about 5 to about 18 wt. %, about 5 to about 15 wt. %, about 5 to about 12 wt. %, about 5 to about 12 wt. %. about 5 to about 10 wt. %, about 10 to about 18 wt. %, or about 10 to about 15 wt. % of the one or more acyl glutamates, based on the total weight of the cleansing composition. In further embodiments, the cleansing composition includes about 0.1 to about 5 wt. %, about 3 to about 8 wt. %, about 5 to about 10 wt. %, about 8 to about 12 wt. %, or about 10 to about 18 wt. % of the one or more acyl glutamates, based on the total weight of the cleansing composition.

(ii) Alkyl Sulfonates

Nonlimiting examples of alkyl sulfonates include alkyl aryl sulfonates, primary alkane disulfonates, alkene sulfonates, hydroxyalkane sulfonates, alkyl glyceryl ether sulfonates, alpha-olefinsulfonates, sulfonates of alkylphenolpolyglycol ethers, alkylbenzenesulfonates, phenylalkanesulfonates, alpha-olefinsulfonates, olefin sulfonates, alkene sulfonates, hydroxyalkanesulfonates and disulfonates, secondary alkanesulfonates, paraffin sulfonates, ester sulfonates, sulfonated fatty acid glycerol esters, and alpha-sulfo fatty acid methyl esters including methyl ester sulfonate.

In some instances, an alkyl sulfonate of formula (VI) is particularly useful.

(VI)

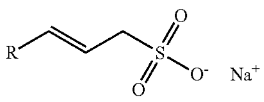

R is selected from H or alkyl chain that has 1-24 carbon atoms, preferably 6-24 carbon atoms, more preferably, 8 to 20 carbon atoms, said chain being saturated or unsaturated, linear or branched. Sodium is shown as the cation in the above formula (III) but the cation may be an alkali metal ion such as sodium or potassium, ammonium ions, or alkanolammonium ions such as monoethanolammonium or triethanolammonium ions. In some instances, the alkyl sulfonate(s) are selected from $C_8$-$C_{16}$ alkyl benzene sulfonates, $C_{10}$-$C_{20}$ paraffin sulfonates, $C_{10}$-$C_{24}$ olefin sulfonates, salts thereof, and combinations thereof. $C_{10}$-$C_{24}$ olefin sulfonates are particularly preferred. A non-limiting but particularly useful example of a $C_{10}$-$C_{24}$ olefin sulfonate that can be used in the instant compositions is sodium C14-16 olefin sulfonate.

The total amount of the one or more alkyl sulfonates in the cleansing composition, if present, will vary. Nonetheless, in certain embodiments, the cleansing composition includes about 0.1 to about 18 wt. % of the one or more alkyl sulfonates, based on a total weight of the cleansing composition. In further embodiments, the cleansing composition includes about 0.1 to about 15 wt. %, about 0.1 to about 12 wt. %, about 0.1 to about 10 wt. %, about 0.1 to about 8 wt. %, about 0.1 to about 5 wt. %, about 0.1 to about 3 wt. %, about 1 to about 18 wt. %, about 1 to about 15 wt. %, about 1 to about 12 wt. %, about 1 to about 10 wt. %, about 1 to about 8 wt. %, about 1 to about 5 wt. %, about 2 to about 18 wt. %, about 2 to about 15 wt. %, about 2 to about 12 wt. %, about 2 to about 10 wt. %, about 2 to about 8 wt. %, about 2 to about 5 wt. %, about 5 to about 18 wt. %, about 5 to about 15 wt. %, about 5 to about 12 wt. %, about 5 to about 12 wt. %. about 5 to about 10 wt. %, about 10 to about 18 wt. %, or about 10 to about 15 wt. % of the one or more alkyl sulfonates, based on the total weight of the cleansing composition. In further embodiments, the cleansing composition includes about 0.1 to about 5 wt. %, about 3 to about 8 wt. %, about 5 to about 10 wt. %, about 8 to about 12 wt. %, or about 10 to about 18 wt. % of the one or more alkyl sulfonates, based on the total weight of the cleansing composition.

(iii) Acyl Isethionates

Non-limiting examples of useful acyl isethionates include those of formula (VII) and (VIII):

(VII)

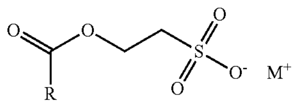

(VIII)

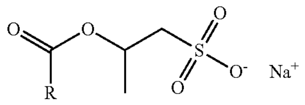

wherein R, $R^1$, $R^2$ and $R^3$ are each independently selected from H or an alkyl chain having 1-24 carbon atoms, said chain being saturated or unsaturated, linear or branched, and X is $COO^-$ or $SO_3^-$. Sodium is shown as the cation in formula (VI) but the cation for both formula (V) and formula (VI) may be an alkali metal ion such as sodium or potassium, ammonium ions, or alkanolammonium ions such as monoethanolammonium or triethanolammonium ions. Non-limiting examples of acyl isethionates include sodium isethionate, sodium cocoyl isethionate, sodium lauroyl methyl isethionate, and sodium cocoyl methyl isethionate. In some instances, sodium cocoyl methyl isethionate is a particularly useful acyl isethionate that may be included in the cleansing compositions.

The total amount of the one or more acyl isethionates in the cleansing composition, if present, will vary. Nonetheless, in certain embodiments, the cleansing composition includes about 0.1 to about 18 wt. % of the one or more acyl isethionates, based on a total weight of the cleansing composition. In further embodiments, the cleansing composition includes about 0.1 to about 15 wt. %, about 0.1 to about 12 wt. %, about 0.1 to about 10 wt. %, about 0.1 to about 8 wt. %, about 0.1 to about 5 wt. %, about 0.1 to about 3 wt. %, about 1 to about 18 wt. %, about 1 to about 15 wt. %, about 1 to about 12 wt. %, about 1 to about 10 wt. %, about 1 to about 8 wt. %, about 1 to about 5 wt. %, about 2 to about 18 wt. %, about 2 to about 15 wt. %, about 2 to about 12 wt. %, about 2 to about 10 wt. %, about 2 to about 8 wt. %, about 2 to about 5 wt. %, about 5 to about 18 wt. %, about 5 to about 15 wt. %, about 5 to about 12 wt. %, about 5 to about 12 wt. %. about 5 to about 10 wt. %, about 10 to about 18 wt. %, or about 10 to about 15 wt. % of the one or more acyl isethionates, based on the total weight of the cleansing composition. In further embodiments, the cleansing composition includes about 0.1 to about 5 wt. %, about 3 to about 8 wt. %, about 5 to about 10 wt. %, about 8 to about 12 wt. %, or about 10 to about 18 wt. % of the one or more acyl isethionates, based on the total weight of the cleansing composition.

(iv) Alkyl Sulfosuccinates

Non-limiting examples of useful alkyl sulfosuccinates include those of formula (IX):

(IX)

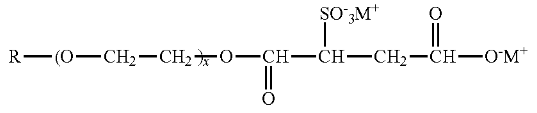

wherein R is a straight or branched chain alkyl or alkenyl group having 10 to 22 carbon atoms, preferably 10 to 20 carbon atoms, X is a number that represents the average degree of ethoxylation and can range from 0 to about 5, preferably from 0 to about 4, and most preferably from about 2 to about 3.5, and M and M' are monovalent cations which can be the same or different from each other. Preferred cations are alkali metal ions such as sodium or potassium, ammonium ions, or alkanolammonium ions such as monoethanolammonium or triethanolammonium ions.

Non-limiting examples of alkyl sulfosuccinates salts include disodium oleamido MIPA sulfosuccinate, disodium oleamido MEA sulfosuccinate, disodium lauryl sulfosuccinate, disodium laureth sulfosuccinate, diammonium lauryl sulfosuccinate, diammonium laureth sulfosuccinate, dioctyl sodium sulfosuccinate, disodium oleamide MEA sulfosuccinate, sodium dialkyl sulfosuccinate, and a combination thereof. In some instances, disodium laureth sulfosuccinate is particularly preferred.

The total amount of the one or more alkyl sulfosuccinates in the cleansing composition, if present, will vary. Nonetheless, in certain embodiments, the cleansing composition includes about 0.1 to about 18 wt. % of the one or more alkyl sulfosuccinates, based on a total weight of the cleansing composition. In further embodiments, the cleansing composition includes about 0.1 to about 15 wt. %, about 0.1 to about 12 wt. %, about 0.1 to about 10 wt. %, about 0.1 to about 8 wt. %, about 0.1 to about 5 wt. %, about 0.1 to about 3 wt. %, about 1 to about 18 wt. %, about 1 to about 15 wt. %, about 1 to about 12 wt. %, about 1 to about 10 wt. %, about 1 to about 8 wt. %, about 1 to about 5 wt. %, about 2 to about 18 wt. %, about 2 to about 15 wt. %, about 2 to about 12 wt. %, about 2 to about 10 wt. %, about 2 to about 8 wt. %, about 2 to about 5 wt. %, about 5 to about 18 wt. %, about 5 to about 15 wt. %, about 5 to about 12 wt. %, about 5 to about 12 wt. %. about 5 to about 10 wt. %, about 10 to about 18 wt. %, or about 10 to about 15 wt. % of the one or more alkyl sulfosuccinates, based on the total weight of the cleansing composition. In further embodiments, the cleansing composition includes about 0.1 to about 5 wt. %, about 3 to about 8 wt. %, about 5 to about 10 wt. %, about 8 to about 12 wt. %, or about 10 to about 18 wt. % of the one or more alkyl sulfosuccinates, based on the total weight of the cleansing composition.

(v) Alkyl Sulfoacetates

Nonlimiting examples of alkyl sulfoacetates includes, for example, alkyl sulfoacetates such as C4-C18 fatty alcohol sulfoacetates and/or salts thereof. A particularly preferred sulfoacetate salt is sodium lauryl sulfoacetate. Useful cations for the salts include alkali metal ions such as sodium or potassium, ammonium ions, or alkanolammonium ions such as monoethanolammonium or triethanolammonium ions.

The total amount of the one or more alkyl sulfoacetates in the cleansing composition, if present, will vary. Nonetheless, in certain embodiments, the cleansing composition includes about 0.1 to about 18 wt. % of the one or more alkyl sulfoacetates, based on a total weight of the cleansing composition. In further embodiments, the cleansing composition includes about 0.1 to about 15 wt. %, about 0.1 to about 12 wt. %, about 0.1 to about 10 wt. %, about 0.1 to about 8 wt. %, about 0.1 to about 5 wt. %, about 0.1 to about 3 wt. %, about 1 to about 18 wt. %, about 1 to about 15 wt. %, about 1 to about 12 wt. %, about 1 to about 10 wt. %, about 1 to about 8 wt. %, about 1 to about 5 wt. %, about 2 to about 18 wt. %, about 2 to about 15 wt. %, about 2 to about 12 wt. %, about 2 to about 10 wt. %, about 2 to about 8 wt. %, about 2 to about 5 wt. %, about 5 to about 18 wt. %, about 5 to about 15 wt. %, about 5 to about 12 wt. %, about 5 to about 12 wt. %. about 5 to about 10 wt. %, about 10 to about 18 wt. %, or about 10 to about 15 wt. % of the one or more alkyl sulfoacetates, based on the total weight of the cleansing composition. In further embodiments, the cleansing composition includes about 0.1 to about 5 wt. %, about 3 to about 8 wt. %, about 5 to about 10 wt. %, about 8 to about 12 wt. %, or about 10 to about 18 wt. % of the one or more alkyl sulfoacetates, based on the total weight of the cleansing composition.

(vi) Alkoxylated Monoacids

Non-limiting examples of alkoxylated monoacids include compounds corresponding to formula (X):

$$RO[CH_2O]_u[(CH_2)_xCH(R')(CH_2)y(CH_2)_zO]_v[CH_2CH_2O]_wCH_2COOH \quad (X)$$

wherein:

R is a hydrocarbon radical containing from about 6 to about 40 carbon atoms;

u, v and w, independently of one another, represent numbers of from 0 to 60;

x, y and z, independently of one another, represent numbers of from 0 to 13;

R' represents hydrogen, alkyl, and the sum of x+y+z>0;

Compounds corresponding to formula (VII) can be obtained by alkoxylation of alcohols ROH with ethylene oxide as the sole alkoxide or with several alkoxides and subsequent oxidation. The numbers u, v, and w each represent the degree of alkoxylation. Whereas, on a molecular level, the numbers u, v and w and the total degree of alkoxylation can only be integers, including zero, on a macroscopic level they are mean values in the form of broken numbers.

In formula (VII), R is linear or branched, acyclic or cyclic, saturated or unsaturated, aliphatic or aromatic, substituted or unsubstituted. Typically, R is a linear or branched, acyclic C6-40 alkyl or alkenyl group or a C1-40 alkyl phenyl group, more typically a C8-22 alkyl or alkenyl group or a C4-18 alkyl phenyl group, and even more typically a C12-18 alkyl group or alkenyl group or a C6-16 alkyl phenyl group; u, v, w, independently of one another, is typically a number from 2 to 20, more typically a number from 3 to 17 and most typically a number from 5 to 15; x, y, z, independently of one another, is typically a number from 2 to 13, more typically a number from 1 to 10 and most typically a number from 0 to 8.

Suitable alkoxylated monoacids include, but are not limited to: Butoxynol-5 Carboxylic Acid, Butoxynol-19 Carboxylic Acid, Capryleth-4 Carboxylic Acid, Capryleth-6 Carboxylic Acid, Capryleth-9 Carboxylic Acid, Ceteareth-25 Carboxylic Acid, Coceth-7 Carboxylic Acid, C9-11 Pareth-6 Carboxylic Acid, C11-15 Pareth-7 Carboxylic Acid, C12-13 Pareth-5 Carboxylic Acid, C12-13 Pareth-8 Carboxylic Acid, C12-13 Pareth-12 Carboxylic Acid, C12-15 Pareth-7 Carboxylic Acid, C12-15 Pareth-8 Carboxylic Acid, C14-15 Pareth-8 Carboxylic Acid, Deceth-7 Carboxylic Acid, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, PPG-6-Laureth-6 Carboxylic Acid, PPG-8-Steareth-7 Carboxylic Acid, Myreth-3 Carboxylic Acid, Myreth-5 Carboxylic Acid, Nonoxynol-5 Carboxylic Acid, Nonoxynol-8 Carboxylic Acid, Nonoxynol-10 Carboxylic Acid, Octeth-3 Carboxylic Acid, Octoxynol-20 Carboxylic Acid, Oleth-3 Carboxylic Acid, Oleth-6 Carboxylic Acid, Oleth-10 Carboxylic Acid, PPG-3-Deceth-2 Carboxylic Acid, Capryleth-2 Carboxylic Acid, Ceteth-13 Carboxylic Acid, Deceth-2 Carboxylic Acid, Hexeth-4 Carboxylic Acid, Isosteareth-6 Carboxylic Acid, Isosteareth-11 Carboxylic Acid, Trudeceth-3 Carboxylic Acid, Trideceth-6 Carboxylic Acid, Trideceth-8 Carboxylic Acid, Trideceth-12 Carboxylic Acid, Trideceth-3 Carboxylic Acid, Trideceth-4 Carboxylic Acid, Trideceth-7 Carboxylic Acid, Trideceth-15 Carboxylic Acid, Trideceth-19 Carboxylic Acid, Undeceth-5 Carboxylic Acid and combinations thereof. In some cases, preferred ethoxylated acids include Oleth-10 Carboxylic Acid, Laureth-5 Carboxylic Acid, Laureth-11 Carboxylic Acid, and a combination thereof.

The total amount of the one or more alkoxylated monoacids in the cleansing composition, if present, will vary. Nonetheless, in certain embodiments, the cleansing composition includes about 0.1 to about 18 wt. % of the one or more alkoxylated monoacids, based on a total weight of the cleansing composition. In further embodiments, the cleansing composition includes about 0.1 to about 15 wt. %, about 0.1 to about 12 wt. %, about 0.1 to about 10 wt. %, about 0.1 to about 8 wt. %, about 0.1 to about 5 wt. %, about 0.1 to about 3 wt. %, about 1 to about 18 wt. %, about 1 to about 15 wt. %, about 1 to about 12 wt. %, about 1 to about 10 wt. %, about 1 to about 8 wt. %, about 1 to about 5 wt. %, about 2 to about 18 wt. %, about 2 to about 15 wt. %, about 2 to about 12 wt. %, about 2 to about 10 wt. %, about 2 to about 8 wt. %, about 2 to about 5 wt. %, about 5 to about 18 wt. %, about 5 to about 15 wt. %, about 5 to about 12 wt. %, about 5 to about 12 wt. %. about 5 to about 10 wt. %, about 10 to about 18 wt. %, or about 10 to about 15 wt. % of the one or more alkoxylated monoacids, based on the total weight of the cleansing composition. In further embodiments, the cleansing composition includes about 0.1 to about 5 wt. %, about 3 to about 8 wt. %, about 5 to about 10 wt. %, about 8 to about 12 wt. %, or about 10 to about 18 wt. % of the one or more alkoxylated monoacids, based on the total weight of the cleansing composition.

(b) Low HLB Nonionic Emulsifiers

Nonionic emulsifiers are known in the art and described in the INCI INGREDIENT DICTIONARY AND HANDBOOK (11th Edition 2006), which is incorporated herein by reference in its entirety. The hydrophilic-lipophilic balance (HLB) of a surfactant is a measure of its degree of hydrophilicity or lipophilicity, determined by calculating percentages of molecular weights for the hydrophilic and lipophilic portions of the surfactant molecule, as described by William C. Griffin, (Calculation of HLB Values of Non-Ionic Surfactants, J. OF THE SOC. OF COSMETIC CHEMISTS, 249-259 (1954)), which is incorporated herein by reference in its entirety.

Nonlimiting examples of nonionic emulsifiers having an HLB of about 6 or less include the following:

1. Sorbitan esters, such as, sorbitan laurate, sorbitan palmitate, sorbitan sesquiisostearate, sorbitan sesquioleate, sorbitan sesquistearate, sorbitan stearate, sorbitan oleate, sorbitan monoisostearate, sorbitan triisostearate, sorbitan trioleate, sorbitan tristearate, and combinations thereof;
2. Glyceryl esters, such as glyceryl behenate, glyceryl caprate, glyceryl caprylate, glyceryl caprylate/caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate, and combinations thereof;
3. Polyglyceryl esters, such as polyglyceryl-4 isostearate, polyglyceryl-3 oleate, polyglyceryl-2 sesquioleate, triglyceryl diisostearate, diglyceryl monooleate, tetraglycerol monooleate, and combinations thereof;
4. Glycol esters, such as glycol distearate, glycol hydroxystearate, glycol oleate, glycol ricinoleate, glycol stearate, propylene glycol isostearate, propylene glycol hydroxystearate, propylene glycol laurate, propylene glycol myristate, propylene glycol oleate, propylene glycol ricinoleate, propylene glycol stearate, and combinations thereof;
5. Sucrose esters, such as sucrose cocoate and sucrose laurate, and combinations thereof
6. Methyl glucose esters, such as methyl glucose sesquistearate, methyl glucose dioleate, and combinations thereof;

Nonlimiting examples of nonionic emulsifier having an HLB of about 6 or less include sucrose distearate, sorbitan stearate, octyldodecyl xyloside, glyceryl stearate, and combinations thereof.

Nonlimiting examples of nonionic emulsifiers having an HLB less than 5 include sorbitan sesquioleate, sorbitan trioleate, sorbitan tristearate, polyethylene sorbitan monostearate, cellulose acetate butyrate, tetradecanol, and combinations thereof.

In a preferred embodiment, the one or more nonionic emulsifiers having an HLB of about 6 or less are selected from glycol esters, glycerol esters, or a combination thereof, for example, one or more selected from glycol distearate, glycol hydroxystearate, glycol oleate, glycol ricinoleate, glycol stearate, propylene glycol isostearate, propylene glycol hydroxystearate, propylene glycol laurate, propylene glycol myristate, propylene glycol oleate, propylene glycol ricinoleate, propylene glycol stearate, diglyceryl polyacyladipate-2, glyceryl behenate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, citrate, glyceryl dioleate, glyceryl distearate, glyceryl laurate, or a combination thereof. In at least one instance the glyceryl ester comprises glyceryl stearate, bis-diglyceryl polyacyladipate, glyceryl ricinoleate, or a combination thereof.

In another preferred embodiment the one or more nonionic emulsifiers have an HLB of about 1 to about 5, such as those selected from glycol distearate, sorbitan trioleate, propylene glycol isostearate, glycol stearate, sorbitan sesquioleate, glyceryl stearate, lecithin, sorbitan oleate, sorbitan monostearate NF, sorbitan Stearate, sorbitan isostearate, steareth-2, oleth-2, or a combination thereof.

| Nonionic Emulsifiers having HLB of About 6 or Less | HLB |
|---|---|
| Ethylene glycol distearate | 1.5 |
| Sorbitan tribleate (Span 85) | 1.8 |
| Sorbitan trioleate (Arlacel 85) | 1.8 |
| Polyoxyethylene sorbitol beeswax derivative (Atlas G-1706) | 2.0 |
| Sorbitan tristearate (Span 65) | 2.1 |
| Sorbitantristearate (Arlacel 65) | 2.1 |
| Polyoxyethylene sorbitol hexastearate (Atlas G-1050) | 2.6 |
| Ethyleneglycol fatty acid ester (Emcol EO-50__ | 2.7 |
| Ethyleneglycol fatty acid ester (Emcol ES-50) | 2.7 |
| Polyoxyethylene sorbitol beeswax derivative (Atlas G-1704) | 3.0 |
| Glyceryl monooleate | 3.3 |
| Propylene glycol monostearate | 3.4 |
| Propylene glycol fatty acid ester (Emcol PO-50) | 3.4 |
| Propylene glycol fatty acid ester (Atlas G-922) | 3.4 |
| "Pure" propylene glycol fatty acid ester | 3.4 |
| Propylene glycol fatty acid ester (Atlas G-2158) | 3.4 |
| Ethylene glycol fatty acid ester (Emcol PS-50) | 3.4 |
| Ethyleneglycol fattyacid ester (Emcol EL-50) | 3.6 |
| Propylene glycol fatty acid ester (Emcol PP-50) | 3.7 |
| Sorbitan sesquioleate (Arlacel C) | 3.7 |
| Sorbitan sesquiolate (Arlacel 83) | 3.7 |
| Polyoxyethyle esorbitol 4,5 oleate (AtlasG-2859) | 3.7 |
| Glycerol monostearate (Atmul 67) | 3.8 |
| Glycerol monostearate (Atmul 84) | 3.8 |
| "Pure" hydroxylatedlanolin | 3.8 |
| Polyoxyethylene sorbitol beeswax | 4.0 |
| Propylene glycol fatty acid ester | 4.1 |
| Sorbitan monoleate (Span 80) | 4.3 |
| Propylene glycol monolaurate (Atlas G-917) | 4.5 |
| Propylene glycol fatty acid ester (EmcolPL-50) | 4.5 |
| Sorbitan monostearate | 4.7 |
| Sorbitan Isostearate | 4.7 |
| Diethylene glycol monooleate (AtlasG-2139) | 4.7 |
| Diethyleneglycol fatty acid ester (Emcol DO-50) | 4.7 |
| Diethylene glycol monostearate (AtlasG-2146) | 4.7 |
| Diethyleneglycol fatty acid ester (Emcol DS-50) | 4.7 |
| Oolyoxyethylene sorbitol beeswax derivative (AtlasG-1702) | 5.0 |
| Diethylene glycol fatty acid ester (Emcol DP-50) | 5.1 |
| Glycerol monostearate | 5.5 |
| Glycerol monostearate | 5.5 |
| Methyl glucoside sesquistearate | 6.0 |
| Diethylene glycol monolaurate (AtlasG-2124) | 6.1 |

The total amount of the one or more nonionic emulsifiers having an HLB of about 6 or less will vary. Nonetheless, in certain embodiments, the cleansing composition includes about 0.1 to about 15 wt. % of the one or more nonionic emulsifiers having an HLB of about 6 or less, based on the total weight of the cleansing composition. In further embodiments, the cleansing compositions includes about 0.1 to about 10 wt. %, about 0.1 to about 5 wt. %, about 0.5 to about 15 wt. %, about 0.5 to about 10 wt. %, about 0.5 to about 5 wt. %, about 1 to about 15 wt. %, about 1 to about 10 wt. %, about 1 to about 8 wt. %, about 1 to about 5 wt. %, about 1 to about 4 wt. %, about 2 to about 15 wt. %, about 2 to about 10 wt. %, about 2 to about 8 wt. %, about 2 to about 5 wt. %, about 2 to about 3 wt. %, about 3 to about 15 wt. %, about 3 to about 10 wt. %, about 3 to about 8 wt. %, about 3 to about 5 wt. %, or about 1 wt. %, about 1.5 wt. %, about 2 wt. %, about 2.5 wt. %, about 3 wt. %, about 3.5 wt. %, about 4 wt. % or about 4.5 wt. % of the one or more nonionic emulsifiers having an HLB of about 6 or less, based on the total weight of the cleansing composition.

(c) Salts Providing a Divalent Cation Source

As mentioned earlier, salts providing a divalent cation source interact synergistically with the anionic polymers to provide a thickening effect and form a lamellar liquid crystal structure. The salts providing a divalent cation typically have a charge density of about 40 to about 200 C/mm$^3$ and a water solubility of at least 400 g/L at 25° C.

Charge density is simply the density of charge around an ion, i.e., the ratio of an ion's charge to its volume. Charge densities (Cmm$^{-3}$) are calculated according to the formula:

$$\frac{ne}{(4/3)\pi r^3}$$

where the ionic radii rare the Shannon-Prewitt values in millimeters, e is the electron charge ($1.60\times10^{-19}$ C), and n represents the ion charge.

Charge densities and methods for calculating charge densities are known in the art. See, e.g., Shannon, Revised Effective Ionic Radii and Systematic Studies of Interatomic Distances in Halides and Chalcogenides, Acta Cryst., A32: 751-767 (1976), which is incorporated herein by reference in its entirety.

As noted above, the salts providing a divalent cation source typically have a charge density of about 40 to about 200 C/mm$^3$. In certain embodiments, the salts providing a divalent cation source have a charge density of about 45 to about 200 C/mm$^3$, about 50 to about 200 C/mm$^3$, about 60 to about 200 C/mm$^3$, about 100 to about 200 C/mm$^3$, about 40 to about 150 C/mm$^3$, about 50 to about 150 C/mm$^3$, about 60 to 150 C/mm$^3$, or about 100 to about 150 C/mm$^3$.

The solubility of salts in water at 25° C. is also well-known, publicly available, and can be easily calculated. The solubility of the salts providing a divalent cation source in the instant case will vary. Nonetheless, in certain embodiments, the salts have a solubility of at least 400 g/L. In further embodiments, the salts have a solubility of at least 450 g/L, at least 500 g/L, or at least 525 g/L.

Nonlimiting examples of salts providing a divalent cation source include magnesium chloride, calcium chloride, magnesium sulfate, magnesium thiosulfate, calcium sulfate, calcium thiosulfate, magnesium pyrrolidone carboxylate (magnesium pidolate), calcium pyrrolidone carboxylate (calcium pidolate), magnesium gluconate, or a combination thereof, preferably wherein the one or more salts providing divalent cations are selected from magnesium chloride, calcium chloride, magnesium sulfate, soluble salts of Mg++, Ca++, calcium sulfate, zinc sulphate, or a combination thereof. In a preferred embodiment, the one or more salts providing divalent cations are selected from the one or more salts providing divalent cations are selected from magnesium chloride, calcium chloride, magnesium sulfate, calcium sulfate, or a combination thereof.

The total amount of the one or more salts providing a divalent cation source will vary. Nonetheless, in certain embodiments, the cleansing composition includes about 0.05 to 5 wt. % of the one or more salts providing a divalent cation source, based on the total weight of the cleansing composition. In further embodiments, the cleansing composition includes about 0.05 to about 4 wt. %, about 0.05 to about 3 wt. %, about 0.05 to about 2 wt. %, about 0.05 to about 1.5 wt. %, about 0.05 to about 1 wt. %, about 0.1 to about 4 wt. %, about 0.1 to about 3 wt. %, about 0.1 to about 2 wt. %, about 0.1 to about 1.5 wt. %, about 0.1 to about 1 wt. %, 0.3 to about 5 wt. %, about 0.3 to about 4 wt. %, about 0.3 to about 3 wt. %, about 0.3 to about 2 wt. %, about 0.3 to about 1.5 wt. %, about 0.3 to about 1 wt. %, about 0.5 to about 5 wt. %, about 0.5 to about 4 wt. %, about 0.5 to about 3 wt. %, about 0.5 to about 2 wt. %, about 0.5 to about 1.5 wt. %, or about 0.5 to about 1 wt. % of the one or more salts providing a divalent cation sources, based on the total weight of the cleansing composition.

(d) Anionic Polymers

In the context of the present disclosure, the term "anionic polymers" is understood as meaning those polymers which carry in a protic solvent under standard conditions at least one structural unit having permanently anionic groups, the anionic groups having to be compensated by counterions while maintaining electroneutrality. As contemplated herein, anionic groups are, for example, carboxylate, sulfate, or sulfonate groups. Nonlimiting examples of anionic polymers include anionic polyurethanes, sodium polynaphthalene sulfonate, sodium lignosulfonate, sodium carboxymethyl cellulose, sodium salt of hydrophobically modified maleic anhydride copolymer, sodium polyacrylate, acrylates copolymer, sodium polymethacrylate, ammonium polyacrylate, ammonium polymethacrylate, sodium salt of polymethacrylic acid, polystyrene sulfonate salts, carrageenan salts, dextran sulfate salts, polyacrylic acid salts, poly(methacrylic acid) salts, alginic acid salts, carboxymethylcellulose salts, polystyrene sulfonate/polystyrene copolymer salts, polystyrene sulfonate/maleic acid copolymers salt, copolymers thereof and combinations thereof.

In various embodiments, the one or more anionic polymers are selected from carboxyvinylpolymers, acrylates copolymers, sulfonate copolymers, and carboxymethylcellulose, and combinations thereof. In various embodiments, the one or more anionic polymers are selected from copolymers of two or more monomers selected from acrylic acid, methacrylic acid, vinyl monomers, and (meth)acrylamide. In an embodiment, the one or more anionic polymers are selected from In an embodiment, the at least one anionic polymer include copolymers of a (meth)acrylic acid and its esters, referred to herein as an (meth)acrylate copolymer. In some embodiments, the copolymer is an acrylates copolymer, which is used herein, refers to a copolymer of two or more monomers selected from the group consisting of acrylic acid, methacrylic acid, and their simple esters, e.g., lower alkyl esters such as methyl, ethyl esters propyl, butyl and pentyl esters. In some embodiments, the polymer refers to a copolymer of two or more monomers selected from the group consisting of acrylic acid, methacrylic acid and vinyl monomers, (meth)acrylamide. Such copolymers, which may be in the form of an aqueous dispersion, are commercially available from numerous sources, including ACUDYNE 180, ACUDYNE BOLD BH Dow Chemical, LUVIFLEX SOFT from BASF, LUVIMER 36D from BASF, DERMACRYL C from Akzo Nobel and SYNTRAN 5760 by Interpolymer. In some embodiments, the acrylates copolymer is an aqueous dispersion consisting of the ethyl ester of acrylic acid and the methyl ester of methacrylic acid, and which is commercially available from Daito Kasei under the tradename DAITOSOL 5000AD.

In various embodiments, the one or more anionic polymer may be be selected from polyacrylate-15, polyacrylate-21, polyacrylate-17, polyacrylate-18, polyacrylate-19, polyacrylate-2 crosspolymer, Acrylates Crosspolymer-3, Polyacrylate-14, Latex Acrylates Copolymer, Styrene/Acrylates/Ammonium Methacrylate Copolymer, Ammonium Acrylates Copolymer, Polyurethane-1, Polyurethane-34, Polyurethane-14/AMP-acrylates copolymer, acrylates copolymers of two or more monomers of (meth)acrylic acid or one of their simple esters, acrylic acid/ethyl acrylate/N-tert-butylacrylamide terpolymers, vinyl acetate/vinyl tert-butylbenzoate/crotonic acid terpolymers, crotonic acid/vinyl acetate/vinyl neodecanoate terpolymers, methyl vinyl ether/monoesterified maleic anhydride copolymers, copolymers of methacrylic acid and of methyl methacrylate, copolymers of methacrylic acid and of ethyl acrylate, vinyl acetate/crotonic acid copolymers, vinyl acetate/crotonic acid copolymers grafted by polyethylene glycol, branched block anionic polymer, Acrylates Crosspolymer-4 acrylates Copolymer, carbomers, acrylates/C10-30 alkyl acrylates crosspolymers, Acrylates/Steareth-20 Methacrylate Crosspolymer, Acrylates/Palmeth-25 Acrylate Copolymer, Acrylates/Palmeth-20 Acrylate Copolymer, octylacrylamide/acrylates/butylamino ethyl (metha)crylate copolymer, acrylic acid/C10-C30 alkyl acrylate crosslinked copolymers, crotonic acid/vinyl acetate/vinyl neodecanoate terpolymers, acrylates copolymer, polyacrylate-2, polyacrylate-21, oxyalkylenated stearyl methacrylate/ethylacrylate/methacrylic acid terpolymer, methacrylic acid/ethyl acrylate/oxyethylenated stearyl methacrylate copolymer (55/35/10); (meth) acrylic acid/ethyl acrylate/25 EO oxyethylenated behenyl methacrylate copolymer, methacrylic acid/ethyl acrylate/steareth-10 allyl ether crosslinked copolymer, an alpha olefin hydrocarbon-maleic anhydride copolymer wax, or combinations thereof.

Additional anionic polymers are included later, in the section entitled, "Additional Thickening Agents." To the extent the thickening agents set forth in the list of thickening agents are anionic polymers, they are incorporated herein by reference in their entirety.

The total amount of the one or more anionic thickening polymer in the cleansing composition will vary. Nonetheless, in certain embodiments, the cleansing composition includes about 0.1 to about 6 wt. % of the one or more anionic polymers, based on the total weight of the cleansing composition. In further embodiments, the cleansing composition includes about 0.1 to about 5 wt. %, about 0.1 to about 4 wt. %, about 0.1 to about 3 wt. %, about 0.1 to about 2 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.8 to about 6 wt. %, bout 0.8 to about 5 wt. %, about 0.8 to about 4 wt. %, about 0.8 to about 3 wt. %, about 0.8 to about 2 wt. %, about 1 to about 6 wt. %, about 1 to about 5 wt. %, about 1 to about 4 wt. %, about 1 to about 3 wt. %, or about 1 to about 2 wt. % of the one or more anionic polymers, based on the total weight of the cosmetic composition.

Ratio of (c) to (d)

The weight ratio of (c) to (d) will vary. Nonetheless, in certain embodiments, the weight ratio of (c) to (d) is about 1:0.5 to about 1:3 (c):(d). In further embodiments, the weight ratio of (d) to (e) is about 1:0.6 to about 1:3, about 1:0.8 to about 1:3, about 1:0.9: to 1:3, about 1:1 to 1:3, about 1:0.5 to about 1:2.5, about 1:0.6 to about 1:2.5, about 1:0.8 to about 1:2.5, about 1:0.9: to 1:25, about 1:1 to 1:1.25, about 1:0.5 to about 1:2, about 1:0.6 to about 1:2, about 1:0.8 to about 1:2, about 1:0.9: to 1:2, about 1:1 to 1:2 ((c):(d)).

(e) Water-Soluble Solvent

The term "water soluble solvent" is interchangeable with the terms "water soluble organic solvent" and "water-miscible solvent" and means a compound that is liquid at 25° C. and at atmospheric pressure (760 mmHg), and has a solubility of at least 50% in water under these conditions. In some cases, the water-soluble solvent has a solubility of at least 60%, 70%, 80%, or 90%. Non-limiting examples of water-soluble solvents include, for example, organic solvents selected from glycerin, alcohols (for example $C_{2-8}$, monoalcohols), polyols (polyhydric alcohols), glycols, and a combination thereof.

Non-limiting examples of water-soluble organic solvents include, for example, organic solvents selected from glycerin, alcohols (for example, $C_{1-10}$, $C_{1-8}$, or $C_{1-4}$ alcohols), polyols (polyhydric alcohols), glycols, and a combination thereof. Nonlimiting examples of monoalcohols and polyols include ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin.

Further non-limiting examples of water soluble organic solvents include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a combination thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a combination thereof. Polyol compounds may also be used. Non-limiting examples include the aliphatic diols, such as 2-ethyl-2-methyl-1,3-propanediol, 3,3-dimethyl-1, 2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a combination thereof.

In a preferred embodiment, the cleansing composition includes glycerin and/or one or more glycols selected from glycerin, propylene glycol, butylene glycol, pentylene glycol, hexylene glycol, caprylyl glycol, dipropylene glycol, a $C_2$-$C_6$ monoalcohol (such as ethanol or isopropanol), and combinations thereof. In an ever preferable embodiment, at least one of the one or more water soluble solvents is glycerin.

The total amount of the one or more water-soluble solvents in the cleansing composition will vary. Nonetheless, in various embodiments, cleansing composition includes about 5 to about 55 wt. % of one or more water soluble solvents, based on the total weight of the hair treatment compositions. In further embodiments, the hair treatment composition includes about 5 to about 50 wt. %, about 5 to about 45 wt. % about 10 to about 55 wt. %, about 10 to about 50 wt. %, about 10 to about 45 wt. %, about 15 to about 55 wt. %, about 15 to about 50 wt. %, about 15 to about 45 wt. %, about 20 to about 55 wt. %, about 20 to about 50 wt. %, about 20 to about 45 wt. %, about 25 to about 55 wt. %, about 25 to about 50 wt. %, about 25 to about 45 wt. %, about 30 to about 55 wt. %, about 30 to about 50 wt. %, or about 30 to about 45 wt. %, based on the total weight of the cleansing composition.

(f) Water

The total amount of water in the cleansing compositions can vary. Nonetheless, in various embodiments, the cleansing composition includes about 15 to about 65 wt. % water based on a total weight of the cleansing composition. In further embodiments, the cleansing composition includes about 15 to about 50 wt. %, about 15 to about 45 wt. %, about 20 to about 65 wt. %, about 20 to about 60 wt. %, about 20 to about 55 wt. %, about 20 to about 50 wt. %, about 20 to about 45 wt. %, about 25 to about 65 wt. %, about 25 to about 60 wt. %, about 25 to about 55 wt. %, about 25 to about 50 wt. %, about 25 to about 45 wt. %, about 30 to about 65 wt. %, about 30 to about 60 wt. %, about 30 to about 55 wt. %, about 30 to about 50 wt. %, about 30 to about 45 wt. %, about 35 to about 65 wt. %, about 35 to about 60 wt. %, about 35 to about 55 wt. %, about 35 to about 50 wt. %, or about 35 to about 45 wt. % of water based on the total weight of the cleansing composition.

Ratio of (e):(f)

The weight ratio of the one or more water soluble solvents of (e) to the water of (f) will vary. Nonetheless, in certain embodiments, the weight ratio of (e) to (f) is about 0.5:1 to 2:1 ((e):(f)). In further embodiments, the weight ratio of (e) to (f) is about 0.5:1 to about 1.8:1, about 0.5:1 to about 1.5:1, about 0.5:1 to about 1.4:1, about 0.6:1 to about 2:1, about 0.6:1 to about 1.8:1, about 0.6:1 to about 1.5:1, about 0.6:1 to about 1.4:1, about 0.7:1 to about 2:1, about 0.7:1.8:1, about 0.7:1 to about 1.5:1, or about 0.7; 1 to about 1.4:1.

(g) Miscellaneous Ingredients

The cleansing compositions may optionally include one more miscellaneous ingredients. Miscellaneous ingredients are ingredients that are compatible with the cleansing compositions and do not disrupt or materially affect the basic and novel properties of the compositions. Nonlimiting examples of miscellaneous ingredients include preservatives, fragrances, pH adjusters, salts, chelating agents, skin active ingredients, buffers, antioxidants, flavonoids, de-pigmenting agents, anti-wrinkle agents, vitamins, botanical extracts, UV filtering agents, proteins, protein hydrolysates and/or isolates, fillers (e.g., organic and/or inorganic fillers such as talc, calcium carbonate, silica, etc.) composition colorants, etc.

In the context of the instant disclosure, a "composition colorant" is a compound that colors the composition but does not have an appreciable coloring effect on hair. In other words, the composition colorant is included to provide a color to the composition for aesthetic appeal but is not intended to impart coloring properties to hair. As an example, hair styling gels, can be found in a variety of different colors (e.g., light blue, light pink, etc.) yet application of the styling gel to hair does not visibly change the color of the hair.

Further nonlimiting examples of antioxidants, skin active agents, depigmenting agents, and anti-wrinkle agents are set forth below.

Antioxidants

Examples of antioxidants include tocopherols (e.g., d-α-tocopherol, d-β-tocopherol, d-γ-tocopherol, d-delta-tocopherol), tocotrienols (e.g., d-α-tocotrienol, d-β-tocotrienol, d-γ-tocotrienol, d-delta-tocotrienol) and vitamin E (α-tocopherol acetate). These compounds may be isolated from natural sources, prepared by synthetic means, or combinations thereof. Tocotrienol-enriched vitamin E preparations may be obtained by fractionating vitamin E preparations to remove a portion of tocopherols and recover a preparation more highly concentrated in tocotrienol. Useful tocotrienols are natural products isolated, for example, from wheat germ oil, grain, or palm oil using high performance liquid chromatography, or isolated by alcohol extraction and/or molecular distillation from barley, brewer's grain or oats. As used herein, the term "tocotrienols" includes tocotrienol-rich-fractions obtained from these natural products as well as the pure compounds. The increased glutathione peroxidase activity protects the skin from oxidative damage.

Vitamin C and derivatives may be used, including ascorbic acid, sodium ascorbate, and the fat soluble esters tetrahexyldecyl ascorbate and ascorbyl palmitate, magnesium ascorbyl phosphate, ascorbyl-glucoside, glucosamine ascorbate, ascorbyl acetate, etc. Additionally, extracts from plants containing a high amount of vitamin C such as camu berry (*Myrciaria dubia*), acerola, *emblica officinalis*, and bioflavonoids from rose hip and citrus may be used including water soluble bioflavonoids such as hesperidin methyl chalcone may also be used.

Sesame (*Sesamum indicum*) or sesame lignan may also be added. Sesame and its lignans (the fibrous compounds associated with the sesame) act as antioxidants. Sesame seed lignans significantly enhance vitamin E activity.

In addition, carotenoids, particularly the xanthophyll type, are also useful antioxidants that can be used. The xanthophyll type carotenoids include molecules, such as lutein, canthaxanthin, cryptoxanthin, zeaxanthin and astaxanthin. Xanthophylls protect compounds, such as vitamin A, vitamin E, and other carotenoids.

Flavonoids can also function as antioxidants. In some instances, the flavonoid is a flavanone (derivative of 2,3-dihydro-2-phenylchromen-4-one). Flavones include: Butin, Eriodictyol, Hesperetin, Hesperidin, Homoeriodictyol, Isosakuranetin, Naringenin, Naringin, Pinocembrin, Poncirin, Sakuranetin, Sakuranin, and Sterebin. The flavonoid may be a flavanonol (derivative of 3-hydroxy-2,3-dihydro-2-phenylchromen-4-one). Flavanols include: Taxifolin, Aromadendrin, Chrysanthoside A, Chrysanthoside B, Xeractinol, Astilbin, and Fustin. The flavonoid may be a flavone (derivative of 2-phenylchromen-4-one). Flavones include: Apigenin, Luteolin, Tangeritin, Chrysin, Baicalein, Scutellarein, Wogonin, Synthetic Flavones: Diosmin, and Flavoxate. The flavonoid may be a flavonol (derivative of 3-hydroxy-2-phenylchromen-4-one). Flavonols include: 3-Hydroxyflavone, Azaleatin, Fisetin, Galangin, Gossypetin, Kaempferide, Kaempferol, Isorhamnetin, Morin, Myricetin, Natsudaidain, Pachypodol, Quercetin, Rhamnazin, Rhamnetin, Azalein, Hyperoside, Isoquercitin, Kaempferitrin, Myricitrin, Quercitrin, Robinin, Rutin, Spiraeoside, Xanthorhamnin, Amurensin, Icariin, and Troxerutin. The flavonoid may be a flavan-3-ol (derivatives of 2-phenyl-3,4-dihydro-2H-chromen-3-ol). Flavan-3-ols include: Catechin, Epicatechin, Epigallocatechin, Epicatechin gallate, Epigallocatechin gallate, Epiafzelechin, Fisetinidol, Guibourtinidol, Mesquitol, and Robinetinidol. The flavonoid may be a flavan-4-ol (derivative of 2-phenylchroman-4-ol). Flavan-4-ols include: Apiforol and Luteoforol. The flavonoid may be an isoflavone (derivative of 3-phenylchromen-4-one). Isoflavones include: Genistein, Daidzein, Biochanin A, Formononetin, and the Equol metabolite from Daidzein.

The antioxidant may be an anthocyanidin (derivative of 2-phenylchromenylium cation). Anthocyanidins include: Aurantinidin, Cyanidin, Delphinidin, Europinidin, Luteolinidin, Pelargonidin, Malvidin, Peonidin, Petunidin, Rosinidin, and Xanthone.

The antioxidant may be a Dihydrochalcone (derivative of 1,3-diphenyl-1-propanone). Dihydrochalcones include: Phloretin, Dihydrochalcone phloretin Phlorizin, Aspalathin, Naringin dihydrochalcone, Neohesperidin dihydrochalcone, and Nothofagin. Without limiting the mode of action of the invention, dihydrochalcones may exert an antioxidant effect by reducing reactive free radicals, like reactive oxygen and reactive nitrogen species.

The antioxidant may be an anthocyanin. Anthocyanins and their derivatives are antioxidants. Anthocyanins encompasses a class of flavonoid compounds that are naturally occurring, water-soluble compounds, responsible for the red, purple, and blue colors of many fruits, vegetables, cereal grains, and flowers. Additionally, anthocyanins are collagenase inhibitors. The inhibition of collagenase helps in the prevention and reduction of wrinkles, increase in skin elasticity, etc., which are caused by a reduction in skin collagen. The anthocyanins may be obtained from any portion of various plant sources, such as the fruit, flower, stem, leaves, root, bark, or seeds. One of skill in the art will understand that certain portions of the plant may contain higher natural levels of anthocyanins, and, therefore, those portions are used to obtain the desired anthocyanins. In some instances, antioxidants may include one or more betacyanin. Betacyanins, like anthocyanins, may be obtained from natural sources and are antioxidants.

The antioxidant may be a Phenylpropanoid (derivatives of cinnamic acid). Phenylpropanoids include: Cinnamic acid, Caffeic acid, Ferulic acid, Trans-ferulic acid (including its antioxidant pharmacore 2,6-dihydroxyacetophenone), 5-Hydroxyferulic acid, Sinapic acid, Coumaryl alcohol, Coniferyl alcohol, Sinapyl alcohol, Eugenol, Chavicol, Safrole, P-coumaric acid, and Sinapinic acid. Without limiting the mode of action of the invention, Phenylpropanoids may neutralize free radicals.

The antioxidant may be a Chalcone (derivative of 1,3-diphenyl-2-propen-1-one). Chalcones include: Butein, Okanin, Carthamin, Marein, Sophoradin, Xanthohumol, Flavokvain A, Flavokavain B, Flavokavin C, and synthetic Safalcone.

The antioxidant may be a Curcuminoid. Curcuminoids include: Curcumin, Desmethoxycurcumin, bis-Desmethoxycurcumin, Tetrahydrocurcumin, and Tetrahydrocurcuminoids. Curcumin and tetrahydrocurcuminoids may be derived from rhizomes of *Curcuma longa*. Tetrahydrocurcumin, a metabolite of curcumin, has been found to be a more potent antioxidant and more stable compared to curcumin.

The antioxidant may be a Tannin. Tannins include: Tannin, Terflavin B, Glucogallin, Dgallic acid, and Quercitannic acid.

The antioxidant may be a stilbenoid. Stilbenoids include: Resveratrol, Pterostilbene, and Piceatannol. Resveratrol may include, but is not limited to, 3,5,4'-trihydroxystilbene, 3,4,3',5'-tetrahydroxystilbene (piceatannol), 2,3',4,5'-tetrahydroxystilbene (oxyresveratrol), 4,4'-dihydroxystilbene, and alpha and beta glucoside, galactoside and mannoside derivatives thereof.

The antioxidant may be a Coumarin (derivatives of 2H-chromen-2-one). Coumarins include: 4-Hydroxycoumarin, Umbelliferone, Aesculetin, Herniarin, Auraptene, and Dicoumarol.

The antioxidant may be a Carotenoid. Carotenoids include: beta-Carotene, alpha-Carotene, gamma-Carotene, beta-Cryptoxanthin, Lycopene, Lutein, and Idebenone. Sesame (*Sesamum indicum*) or sesame lignan may also be added. Sesame and its lignans (the fibrous compounds associated with the sesame) act as antioxidants. Sesame seed lignans significantly enhance vitamin E activity.

The antioxidant may be: a Xanthone, Butylated Hydroxytoluene, 2,6-Di-tert-butylphenol, 2,4-Dimethyl-6-tert-butylphenol, Gallic acid, Eugenol, Uric acid, alpha-Lipoic acid, Ellagic acid, Chicoric acid, Chlorogenic acid, Rosmarinic acid, Salicylic acid, Acetylcysteine, S-Allyl cysteine, Barbigerone, Chebulagic acid, Edaravone, Ethoxyquin, Glutathione, Hydroxytyrosol, Idebenone, Melatonin, N-Acetylserotonin, Nordihydroguaiaretic acid, Oleocanthal, Oleuropein, Paradol, Piceatannol, Probucol, Propyl gallate, Protocatechuic acid, Pyritinol, Rutin, Secoisolariciresinol diglucoside, Sesamin, Sesamol, Silibinin, Silymarin, Theaflavin, Theaflavin digallate, Thymoquinone, Trolox, Tyrosol, Polyunsaturated fatty acids, and sulfur-based antioxidants such as Methionine or Lipoic acid.

Skin Active Agents

Nonlimiting examples of skin active agents include hydroxyacetophenone, madecassoside, retinoic acid, benzoyl peroxide, sulfur, vitamin B6 (pyridoxine or) chloride, selenium, samphire—the cinnamon extract blends, tea and octanoylglycine such as—15 Sepicontrol A5 TEA from Seppic—the mixture of cinnamon, sarcosine and octanoylglycine marketed especially by Seppic under the trade name Sepicontrol A5—zinc salts such as zinc gluconate, zinc pyrrolidinecarboxylate (or zinc pidolate), zinc lactate, zinc aspartate, zinc carboxylate, zinc salicylate 20, zinc cysteate; —derivatives particularly copper and copper pidolate as Cuivridone Solabia—extracts from plants of *Arnica montana, Cinchona succirubra, Eugenia caryophyllata, Humulus lupulus, Hypericum perforatum, Mentha pipenta* 25 *Rosmarinus officinalis, Salvia officinalis* and *Thymus vulgaris*, all marketed for example by Maruzen—extracts of meadowsweet (*Spiraea ulmaria*), such as that sold under the name Sebonormine by Silab—extracts of the alga *Laminaria saccharina*, such as that sold under the 30 name Phlorogine by Biotechmarine—the root extracts of burnet mixtures (Sanguisorba *officinalis/Poterium officinale*), rhizomes of ginger (*Zingiber officinalis*) and cinnamon bark (*Cinnamomum cassia*), such as that sold under the name Sebustop by Solabia—extracts of flaxseed such as that sold under the name Linumine by Lucas Meyer—*Phellodendron* extracts such as those sold under the name *Phellodendron* extract BG by Maruzen or Oubaku liquid B by Ichimaru Pharcos—of argan oil mixtures extract of Serenoa *serrulata* (saw palmetto) extract and sesame seeds such as that sold under the name Regu SEB by Pentapharm—mixtures of extracts of willowherb, of *Terminalia chebula, nasturtium* and of bioavailable zinc (microalgae), such as that sold under the name Seborilys Green Tech; —extracts of *Pygeum afrianum* such as that sold under the name *Pygeum afrianum* sterolic lipid extract by Euromed—extracts of Serenoa *serrulata* such as those sold under the name Viapure Sabal by Actives International, and those sold by the company Euromed—of extracts of plantain blends, *Berberis aquifolium* and sodium salicylate 20 such as that sold under the name Seboclear Rahn—extract of clove as that sold under the name Clove extract powder by Maruzen—argan oil such as that sold under the name Lipofructyl Laboratories Serobiologiques; 25—lactic protein filtrates, such as that sold under the name Normaseb by Sederma—the seaweed *laminaria* extracts, such as that sold under the name Laminarghane by Biotechmarine—oligosaccharides seaweed *Laminaria* digitata, such as that sold under the name Phycosaccharide 30 AC by the company Codif—extracts of sugar cane such as that sold under the name Policosanol by the company Sabinsa, the sulfonated shale oil, such as that sold under the name Ichtyol Pale by Ichthyol—extracts of meadowsweet (*Spiraea ulmaria*) such as that sold under the name Cytobiol Ulmaire by societeLibiol—sebacic acid, especially sold in the form of a sodium polyacrylate gel under the name Sebosoft by Sederma—glucomannans extracted from konjac tuber and modified with alkylsulfonate chains such as that sold under the name Biopol Beta by Arch Chemical—extracts of *Sophora angustifolia*, such as those sold under the name *Sophora* powder or *Sophora* extract by Bioland—extracts of *cinchona* bark succirubra such as that sold under the name Red Bark HS by Alban Muller—extracts of *Quillaja saponaria* such as that sold under the name 15 *Panama* wood HS by Alban Muller—glycine grafted onto an undecylenic chain, such as that sold under the name Lipacide UG OR by SEPPIC—the mixture of oleanolic acid and nordihydroguaiaretic acid, such as that sold under the form of a gel under the name AC.Net by Sederma; 20—phthalimidoperoxyhexanoic acid—citrate tri (C12-C13) sold under the name COSMACOL™ ECI by Sasol; trialkyl citrate (C14-C15) sold under the name COSMACOL™ ECL by Sasol—10-hydroxydecanoic acid, including mixtures acid-hydroxydecanoic October 25, sebacic acid and 1,10-decanediol such as that sold under the name Acnacidol BG by Vincience and combinations thereof.

Depigmenting Agents

Nonlimiting examples of depigmenting agents include alpha and beta arbutin, ferulic acid, leucinol and its derivatives, kojic acid, resorcinol and derivatives thereof, tranexamic acid and derivatives thereof, gentisic acid, homogentisic, methyl gentisate or homogentisate, dioic acid, D pantetheine calcium sulphonate, lipoic acid, ellagic acid, vitamin B3, linoleic acid and its derivatives, certain compounds derived from plants such as chamomile, bearberry, the aloe family (*vera, ferox, bardensis*), mulberry, skullcap, a water kiwi fruit (*Actinidia chinensis*) marketed by Gattefosse, an extract of *Paeonia suffruticosa* root, such as that sold by Ichimaru Pharcos under the name Liquid Botanpi Be an extract of brown sugar (*Saccharum officinarum*) such as molasses extract marketed by Taiyo Kagaku under the name Liquid Molasses, without this list being exhaustive. Particular depigmenting agents include alpha and beta arbutin, ferulic acid, kojic acid, resorcinol and derivatives, D pantetheine calcium sulfonate, lipoic acid, ellagic acid, vitamin B3, a water kiwi fruit (*Actinidia chinensis*) marketed by Gattefosse, an extract of *Paeonia suffruticosa* root, such as that sold by the company Ichimaru Pharcos under the name Botanpi Liquid B.

Anti-Wrinkle Agent

The term "anti-wrinkle agent" refers to a natural or synthetic compound producing a biological effect, such as the increased synthesis and/or activity of certain enzymes, when brought into contact with an area of wrinkled skin, this has the effect of reducing the appearance of wrinkles and/or fine lines. Nonlimiting examples of anti-wrinkle agents include: desquamating agents, anti-glycation agents, inhibitors of NO-synthase, agents stimulating the synthesis of dermal or epidermal macromolecules and/or preventing their degradation, agents for stimulating the proliferation of fibroblasts and/or keratinocytes, or for stimulating keratinocyte differentiation reducing agents; muscle relaxants and/or dermo-decontracting agents, anti-free radical agents, and combinations thereof. Examples of such compounds are: adenosine and its derivatives and retinoids other than retinol (as discussed above, such as retinol palmitate), ascorbic acid and its derivatives such as magnesium ascorbyl phosphate and ascorbyl glucoside; nicotinic acid and its precursors such as nicotinamide; ubiquinone; glutathione and precursors thereof such as L-2-oxothiazolidine-4-carboxylic acid, the compounds C-glycosides and their derivatives as described in particular in EP-1345919, in particular C-beta-D-xylopyranoside-2-hydroxy-propane as described in particular in EP-1345919, plant extracts including sea fennel and extracts of olive leaves, as well as plant and hydrolysates thereof such as rice protein hydrolysates or soybean proteins; algal extracts and in particular *laminaria*, bacterial extracts, the sapogenins such as diosgenin and extracts of *Dioscorea* plants, in particular wild yam, comprising: the α-hydroxy acids, b-hydroxy acids, such as salicylic acid and n-octanoyl-5-salicylic oligopeptides and pseudodipeptides and acyl derivatives thereof, in particular acid {2-[acetyl-(3-trifluoromethyl-phenyl)-amino]-3-methyl-}acetic acid and lipopeptides marketed by the company under the trade names SEDERMA Matrixyl 500 and Matrixyl 3000; lycopene, manganese salts and magnesium salts, especially gluconates, and combinations thereof. In at least one case, the skin tightening composition includes adenosine derivatives, such as non-phosphate derivatives of adenosine, such as in particular the 2'-deoxyadenosine, 2',3'-adenosine isopropylidene; the toyocamycin, 1-methyladenosine, N-6-methyladenosine; adenosine N-oxide, 6-methylmercaptopurine riboside, and the 6-chloropurine riboside. Other derivatives include adenosine receptor agonists such as adenosine phenylisopropyl ("PIA"), 1-methylisoguanosine, N6-cyclohexyladenosine (CHA), N6-cyclopentyladenosine (CPA), 2-chloro-N6-cyclopentyladenosine, 2-chloroadenosine, N6-phenyladenosine, 2-phenylaminoadenosine, MECA, N 6-phenethyladenosine, 2-p-(2-carboxy-ethyl) phenethyl-amino-5'-N-ethylcarboxamido adenosine (CGS-21680), N-ethylcarboxamido-adenosine (NECA), the 5'(N-cyclopropyl)-carboxamidoadenosine, DPMA (PD 129.944) and metrifudil.

As already noted, skin active agents may be included as one or more of the miscellaneous ingredients. With respect to the total amount of skin active agents in the cosmetic compositions, if present, the total amount of skin active agents may be from greater than zero to about 9 wt. %, greater than zero to about 8 wt. %, greater than zero to about 7 wt. %, greater than zero to about 6 wt. %, greater than zero to about 5 wt. %, greater than zero to about 4 wt. %, greater than zero to about 3 wt. %, greater than zero to about 2 wt. %; about 10 ppm to about 10 wt. % (100,000 ppm), about 10 ppm to about 5 wt. % (50,000 ppm), about 10 ppm to about 2.5 wt. % (25,000 ppm), about 10 ppm to about 1 wt. % (10,000 ppm), about 10 ppm to about 0.5 wt. % (5,000 ppm), about 10 ppm to about 0.3 wt. % (3,000 ppm), about 10 ppm to about 0.2 wt. % (2,000 ppm), about 10 ppm to about 0.1 wt. % (1,000 ppm), about 10 ppm to 500 ppm; about 0.1 to about 10 wt. %, about 0.1 to about 5 wt. %, about 0.1 to about 2.5 wt. %, about 0.1 to about 1 wt. %, about 0.1 to about 0.5 wt. %; about 1 to about 10 wt. %, about 1 to about 8 wt. %, about 1 to about 6 wt. %, about 1 to about 5 wt. %, about 1 to about 4 wt. %, about 1 to about 3 wt. %; about 2 to about 10 wt. %, about 2 to about 8 wt. %, about 2 to about 6 wt. %, about 2 to about 5 wt. %, about 2 to about 4 wt. %; about 3 to about 10 wt. %, about 3 to about 8 wt. %, about 3 to about 6 wt. %, about 3 to about 5 wt. %; about 4 to about 10 wt. %, about 4 to about 8 wt. %, or about 4 to about 6 wt. %, based on the total weight of the cosmetic composition.

The total amount of the one or more miscellaneous ingredients, if present, will vary. Nonetheless, in various embodiments, the compositions include from about 0.001 to about 10 wt. % of one or more miscellaneous ingredients, based on the total weight of the composition. In further embodiments, the compositions include from about 0.001 to about 5 wt. %, about 0.001 to about 3 wt. %, about 0.01 to about 10 wt. %, about 0.01 to about 5 wt. %, about 0.01 to about 3 wt. %, about 0.1 to about 10 wt. %, about 0.1 to about 5 wt. %, or about 0.1 to about 3 wt. % of one or more miscellaneous ingredients, based on the total weight of the composition.

Additional Embodiments

The cleansing compositions do not require amphoteric surfactants and therefore, in certain embodiments, the cleansing composition may be free or essentially free from amphoteric surfactants. In other embodiments, however, it is preferable to include one or more amphoteric surfactants. Nonlimiting examples of amphoteric surfactants and amounts are provided below, under the heading "Amphoteric Surfactants."

The cleansing compositions do not require nonionic surfactants or nonionic emulsifiers other than the one or more nonionic emulsifiers of having a Hydrophile-Lipophile Balance (HLB) of about 6 or less of (b). Therefore, in certain embodiments, the cleansing compositions may be free or essentially free from nonionic surfactants and emulsifiers other than the one or more nonionic emulsifiers of having a Hydrophile-Lipophile Balance (HLB) of about 6 or less of (b). In other embodiments, however, it is preferable to include one or more nonionic surfactants or nonionic emulsifiers having an HLB greater than 6. Nonlimiting examples of nonionic surfactants and amounts are provided below, under the heading "Nonionic Surfactants."

The one or more salts providing a providing divalent cation source and the one or more anionic polymers interact to provide a thickening effect to the cleansing compositions such that the cleansing compositions do not require additional thickening agents. Therefore, the cleansing compositions may be free or essentially free from additional thickening agents. Nonetheless, in certain embodiments, it is preferable to include one or more additional thickening agents. Nonlimiting examples of additional thickening agents are provided below, under the heading "Additional Thickening Agents." To the extent the additional thickening agents include anionic polymers, the anionic polymers are considered an anionic polymer of (d), even if they are known to independently provide thickening or known to be a thickening agent.

The cleansing composition of the instant case do not require non-silicone fatty compounds. Therefore, the compositions may be free or essentially free from non-silicone fatty compounds. Nonetheless, in various preferred embodiments, the cleansing composition may include one or more non-silicone fatty compounds. Nonlimiting examples and amounts of non-silicone fatty compounds is provided under the heading "Non-Silicone Compounds."

The cleansing compositions do not require silicones, including amino-functionalized silicones. Therefore, the cleansing compositions may be free or essentially free from silicones including amino-functionalized silicone. However, in certain embodiments, the cleansing compositions may include one or more silicones. Nonlimiting examples of silicones include dimethicone, dimethiconol, cyclomethicone, polysilicone-11, phenyl trimethicone, trimethylsilylamodimethicone, and stearoxytrimethylsilane. In some instances, the cleansing composition includes or excludes (or essentially excludes) one or more silicones silicon oils. Nonlimiting examples of silicone oils include polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl) trimethylsiloxysilicates. Other examples of silicone oils that may be mentioned include volatile linear or cyclic silicones, such as those with a viscosity 8 centistokes (8×106 m2/s) and/or containing from 2 to 7 silicon atoms. These silicones optionally comprise alkyl or alkoxy groups containing from 1 to 10 carbon atoms. Non-limiting examples of volatile silicone oils include octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, or combinations thereof. In various embodiments, the hair treatment compositions include one or more silicone oils chosen from dimethicone, dimethiconol, cyclomethicone, polysilicone-11, phenyl trimethicone, and amodimethicone, and a combination thereof. If present, the amount of the one or more silicones is less than 5 wt. %, preferably less than 3 wt. %. For example, the cleansing composition may include about 0.01 to about 5, about 0.01 to about 4, about 0.01 to about 3, about 0.01 to about 2, or about 0.01 to about 1 wt. % of one or more silicones. Further, the cleansing composition may include less than 1 wt. % of silicones, less than 0.5 wt.

% of silicones, less than 0.1 wt. % of silicones, less than 0.05 wt. % of silicones, or be free from silicones.

Amphoteric Surfactants

Nonlimiting examples of amphoteric surfactants include alkyl amphopropionates, betaines, alkyl sultaines, alkyl amphoacetates, and combinations thereof. In some instances, it is preferable to include one or more alkyl betaines.

Alkyl Amphopropionates

In some instances, the cleansing compositions preferably include one or more alkyl amphopropionates. Non-limiting examples of alkyl amphopropionates include cocoamphopropionate, cornamphopropionate, caprylamphopropionate, cornamphopropionate, caproamphopropionate, oleoamphopropionate, isostearoamphopropionate, stearoamphopropionate, lauroamphopropionate, salts thereof, and a combination thereof. Sodium cocoamphopropionate is a particularly useful alkyl amphopropionate that can be included in the cleansing compositions.

The total amount of alkyl amphopropionates in the cleansing composition, if present, may vary but is typically from about 0.01 to about 15 wt. %, based on the total weight of the cleansing composition. In some instance, the total amount of amphopropionates in the cleansing composition is from about 0.01 to about 15 wt. %, about 0.01 to about 10 wt. %, about 0.01 to about 5 wt. %, about 0.1 to about 20 wt. %, about 0.1 to about 15 wt. %, or about 0.1 to about 10 wt. %, about 0.1 to about 5 wt. %, about 0.1 to about 3 wt. % based on the total weight of the cleansing composition.

Betaines

Useful betaines include those of the following formulae (XIa-XId):

(XIa)

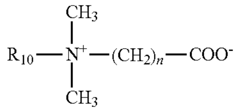

(XIb)

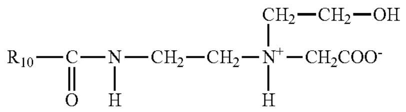

(XIc)

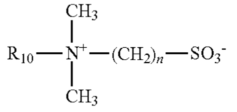

(XId)

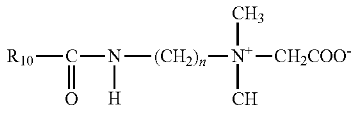

wherein $R_{10}$ is an alkyl group having 8-18 carbon atoms; and n is an integer from 1 to 3.

Particularly useful betaines include, for example, coca betaine, cocamidopropyl betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, and combinations thereof. Typically, at least one betaine compound is selected from coco betaine, cocamidopropyl betaine, behenyl betaine, capryl/capramidopropyl betaine, and lauryl betaine, and combinations thereof. Particularly preferred betaines include coco betaine and cocamidopropyl betaine.

In a preferred embodiment, the cleansing composition includes at least one betaine, preferably at least two betaines.

The total amount of the one or more betaine surfactants in the cleansing compositions, if present, will vary but is typically from about 0.1 to about 15 wt. %, based on the total weight of the cleansing composition. In some instance, the total amount of one or more betaines in the cleansing composition is from about 0.1 to about 10 wt. %, from about 0.1 to about 8 wt. %, from about 0.1 to about 5 wt. %, from about 0.1 to about 3 wt. %, about 1 to about 15 wt. %, about 1 to about 10 wt. %, about 1 to about 8 wt. %, about 1 to about 5 wt. %, or 2 to about 15 wt. %, about 2 to about 10 wt. %, or about 2 to about 8 wt. %, about 4 to about 15 wt. %, about 4 to about 12 wt. %, about 4 to about 10 wt. %, about 4 to about 8 wt. %, about 5 to about 15 wt. %, about 5 to about 12 wt. %, or about 5 to about 10 wt. %, based on the total weight of the cleansing composition.

Alkyl Sultaines

Non-limiting examples of alkyl sultaines include hydroxyl sultaines of formula (XI)

(XI)

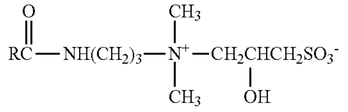

wherein R is an alkyl group having 8-18 carbon atoms. More specific examples include, but are not limited to cocamidopropyl hydroxysultaine, lauryl hydroxysultaine, and a combination thereof.

The total amount of alkyl sultaines in the cleansing composition, if present, may vary but is typically from about 0.01 to about 20 wt. %, based on the total weight of the cleansing composition. In some instance, the total amount of alkyl sultaines in the cleansing composition is from about 0.01 to about 15 wt. %, from about 0.01 to about 10 wt. %, from about 0.01 to about 5 wt. %, from about 0.1 to about 15 wt. %, from about 0.1 to about 10 wt. %, from about 0.1 to about 5 wt. %, based on the total weight of the cleansing composition.

Alkyl Amphoacetates and Alkyl Amphodiacetates

Useful alkyl amphoacetates and alkyl amphodiacetates include those of Formula (XII) and (XIII):

(XII)

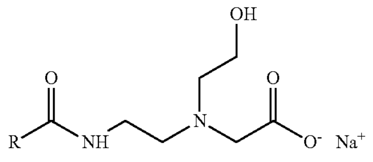

(XIII)

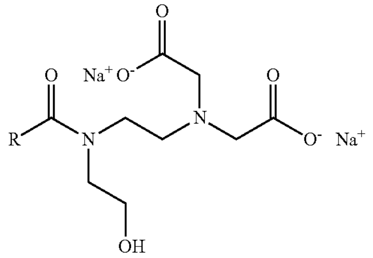

wherein R is an alkyl group having 8-18 carbon atoms. Sodium is shown as the cation in the above formulae above but the cation may be an alkali metal ion such as sodium or potassium, ammonium ions, or alkanolammonium ions such as monoethanolammonium or triethanolammonium ions. A more specific, but non-limiting example, is sodium lauroamphoacetate.

The total amount of alkyl amphoacetates and/or alkyl amphodiacetates in the cleansing composition, if present, may vary but is typically from about 0.01 to about 20 wt. %, based on the total weight of the cleansing composition. In some instance, the total amount of alkyl amphoacetates and/or alkyl amphodiacetates in the cleansing composition is from about 0.01 to about 15 wt. %, from about 0.01 to about 10 wt. %, from about 0.01 to about 5 wt. %, from about 0.1 to about 15 wt. %, from about 0.1 to about 10 wt. %, from about 0.1 to about 5 wt. %, based on the total weight of the cleansing composition.

The total amount of the one or more amphoteric surfactant (s) in the cleansing compositions will vary but is typically from about 0.1 to about 20 wt. %, based on the total weight of the cleansing composition. In some instance, the total amount of amphoteric surfactant(s) in the cleansing composition is from about 0.1 to about 15 wt. %, from about 0.1 to about 10 wt. %, from about 0.1 to about 8 wt. %, from about 1 to about 20 wt. %, about 1 to about 15 wt. %, about 1 to about 10 wt. %, about 1 to about 8 wt. %, or 2 to about 15 wt. %, about 2 to about 10 wt. %, or about 2 to about 8 wt. %, about 4 to about 20 wt. %, about 4 to about 15 wt. %, about 4 to about 12 wt. %, about 4 to about 10 wt. %, about 4 to about 8 wt. %, about 5 to about 20 wt. %, about 5 to about 15 wt. %, about 5 to about 12 wt. %, or about 5 to about 10 wt. %, based on the total weight of the cleansing composition.

Nonionic Surfactants

The cleansing compositions include one or more nonionic surfactants, preferably a plurality of nonionic surfactants. Non-limiting examples of nonionic surfactants include: alkanolamides; alkyl polyglucosides; polyoxyalkylenated nonionic surfactants; polyglycerolated nonionic surfactants; ethoxylated fatty esters; alcohols, alpha-diols, alkylphenols and esters of fatty acids, being ethoxylated, propoxylated or glycerolated; copolymers of ethylene oxide and/or of propylene oxide; condensates of ethylene oxide and/or of propylene oxide with fatty alcohols; polyethoxylated fatty amides; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and combinations thereof.

(i) Alkanolamides

Non-limiting examples alkanolamides include fatty acid alkanolamides. The fatty acid alkanolamides may be fatty acid monoalkanolamides or fatty acid dialkanolamides or fatty acid isoalkanolamides, and may have a $C_{2-8}$ hydroxyalkyl group (the $C_{2-8}$ chain can be substituted with one or more than one —OH group). Non-limiting examples include fatty acid diethanolamides (DEA) or fatty acid monoethanolamides (MEA), fatty acid monoisopropanolamides (MIPA), fatty acid diisopropanolamides (DIPA), and fatty acid glucamides (acyl glucamides).

Suitable fatty acid alkanolamides include those formed by reacting an alkanolamine and a C6-C36 fatty acid. Examples include, but are not limited to: oleic acid diethanolamide, myristic acid monoethanolamide, soya fatty acids diethanolamide, stearic acid ethanolamide, oleic acid monoisopropanolamide, linoleic acid diethanolamide, stearic acid monoethanolamide (Stearamide MEA), behenic acid monoethanolamide, isostearic acid monoisopropanolamide (isostearamide MIPA), erucic acid diethanolamide, ricinoleic acid monoethanolamide, coconut fatty acid monoisopropanolamide (cocoamide MIPA), coconut acid monoethanolamide (Cocamide MEA), palm kernel fatty acid diethanolamide, coconut fatty acid diethanolamide, lauric diethanolamide, polyoxyethylene coconut fatty acid monoethanolamide, coconut fatty acid monoethanolamide, lauric monoethanolamide, lauric acid monoisopropanolamide (lauramide MIPA), myristic acid monoisopropanolamide (Myristamide MIPA), coconut fatty acid diisopropanolamide (cocamide DIPA), and combinations thereof.

In some instances, the fatty acid alkanolamides preferably include cocamide MIPA, cocamide DEA, cocamide MEA, cocamide DIPA, and combinations thereof. In particular, the fatty acid alkanolamide may be cocamide MIPA, which is commercially available under the tradename EMPILAN from Innospec Active Chemicals.

Fatty acid alkanolamides include those of the following structure:

$$\overset{O}{\overset{\|}{R_4C}}NR_5R_6 \qquad (XIV)$$

wherein $R_4$ is an alkyl chain of 4 to 20 carbon atoms ($R_4$ may be, for example, selected from lauric acid, coconut acid, palmitic acid, myristic acid, behenic acid, babassu fatty acid, isostearic acid, stearic acid, corn fatty acid, soy fatty acid, shea butter fatty acids, caprylic acid, capric acid, and combinations thereof);

$R_6$ is selected from $-CH_2OH$, $-CH_2CH_2OH$, $-CH_2CH_2CH_2OH$, $-CH_2(CHOH)_4CH_2OH$, -benzyl, and combinations thereof;

$R_6$ is selected from $-H$, $-CH_3$, $-CH_2OH$, $-CH_2CH_3$, $-CH_2CH_2OH$, $-CH_2CH_2CH_2OH$, $-CH_2(CHOH)_4CH_2OH$, -benzyl, and combinations thereof.

In some instances, the one or more of the fatty acid alkanolamides include one or more acyl glucamides, for example, acyl glucamides having a carbon chain length of 8 to 20. Non-limiting examples include lauroyl/myristoyl methyl glucamide, capryloyl/capryl methyl glucamide, lauroyl methyl glucamide, myristoyl methyl glucamide, capryloyl methyl glucamide, capryl methyl glucamide, cocoyl methyl glucamide, capryloyl/caproyl methyl glucamide, cocoyl methyl glucamide, lauryl methylglucamide, oleoyl methylglucamide oleate, stearoyl methylglucamide stearate, sunfloweroyl methylglucamide, and tocopheryl succinate methylglucamide.

The total amount of alkanolamides in the cleansing compositions, if present, can vary but is typically about 0.1 to about 15 wt. %, based on the total weight of the cleansing composition. In some instances, the total amount of alkanolamides is about 0.1 to about 10 wt. %, about 0.1 to about 8 wt. %, about 0.1 to about 5 wt. %, about 0.1 to about 3 wt. %, about 0.5 to about 15 wt. %, about 0.5 to about 12 wt. %, about 0.5 to about 10 wt. %, about 0.5 to about 8 wt. %, about 0.5 to about 5 wt. %, based on a total weight of the cleansing composition.

(ii) Alkyl Polyglucosides

Useful alkyl polyglucosides include those having the following formula (XV):

$$R^1-O-(R^2O)_n-Z(X) \qquad (XV)$$

wherein $R^1$ is an alkyl group having 8-18 carbon atoms;

$R^2$ is an ethylene or propylene group;

Z is a saccharide group with 5 to 6 carbon atoms;

n is an integer from 0 to 10; and x is an integer from 1 to 5.

Useful alkyl poly glucosides include lauryl glucoside, octyl glucoside, decyl glucoside, coco glucoside, caprylyl/capryl glucoside, and sodium lauryl glucose carboxylate. Typically, the at least one alkyl poly glucoside compound is selected from the group consisting of lauryl glucoside, decyl glucoside and coco glucoside. In some instances, decyl glucoside is particularly preferred.

The total amount of alkyl polyglucosides in the cleansing compositions, if present, can vary but is typically about 0.0 to about 15 wt. %, based on the total weight of the cleansing compositions. In some instances, the total amount of alkyl polyglucosides is about 0.1 to about 10 wt. %, about 0.1 to about 8 wt. %, about 0.1 to about 5 wt. %, about 0.1 to about 3 wt. %, about 0.5 to about 15 wt. %, about 0.5 to about 12 wt. %, about 0.5 to about 10 wt. %, about 0.5 to about 8 wt. %, about 0.5 to about 5 wt. %, based on a total weight of the cleansing composition.

(iii) Additional Nonionic Surfactants

Nonionic surfactants also include, for example, alcohols, alpha-diols, alkylphenols and esters of fatty acids, being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and combinations thereof.

Such nonionic surfactants may preferably be chosen from polyoxyalkylenated or polyglycerolated nonionic surfactants. The oxyalkylene units are more particularly oxyethylene or oxypropylene units, or a combination thereof, and are preferably oxyethylene units.

In some cases, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and combinations thereof.

Examples of ethoxylated fatty esters that may be mentioned include the adducts of ethylene oxide with esters of lauric acid, palmitic acid, stearic acid or behenic acid, and combinations thereof, especially those containing from 9 to 100 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and combinations thereof.

As glyceryl esters of fatty acids, glyceryl stearate (glyceryl mono-, di- and/or tristearate) (CTFA name: glyceryl stearate) or glyceryl ricinoleate and combinations thereof can in particular be cited.

As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited.

Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEG1 N by Goldschmidt (CTFA name: glyceryl stearate SE), can also be used.

The total amount of additional nonionic surfactants (nonionic surfactants other than alkanolamides and alkyl polyglucosides) in the cleansing compositions, if present, can vary but is typically about 0.1 to about 15 wt. %, based on the total weight of the cleansing composition. In some instances, the total amount of additional nonionic surfactants is about 0.1 to about 10 wt. %, about 0.1 to about 8 wt. %, about 0.1 to about 5 wt. %, about 0.1 to about 3 wt. %, about 0.5 to about 15 wt. %, about 0.5 to about 12 wt. %, about 0.5 to about 10 wt. %, about 0.5 to about 8 wt. %, about 0.5 to about 5 wt. %, based on a total weight of the cleansing composition.

The total amount of all nonionic surfactants can vary but is typically about 0.1 to about 20 wt. %, based on the total weight of the cleansing compositions. In some cases, the total amount of nonionic surfactants is about 0.1 to about 15 wt. %, about 0.1 to about 12 wt. %, about 0.1 to about 10 wt. %, about 0.1 to about 8 wt. %, about 1 to about 20 wt. %, about 1 to about 15 wt. %, about 1 to about 12 wt. %, about 1 to about 10 wt. %, about 1 to about 8 wt. %, about 2 to about 20 wt. %, about 2 to about 15 wt. %, about 2 to about 12 wt. %, about 2 to about 10 wt. %, about 2 to about 8 wt. %, about 3 to about 10 wt. %, or about 3 to about 8 wt. %, based on the total weight of the cleansing composition.

Additional Thickening Agents

The cleansing compositions may optionally include one or more thickening agents (also referred to as thickeners or viscosity modifying agents). Many thickening agents are water soluble and increase the viscosity of water or form an aqueous gel when dispersed/dissolved in water. The aqueous solution may be heated and cooled, or neutralized, for forming the gel, if necessary. The thickening agent may be dispersed/dissolved in an aqueous solvent that is soluble in water, e.g., ethyl alcohol when it is dispersed/dissolved in water.

The following lists of various thickening agents overlaps with the one or more anionic polymers of (d). To the extent a thickening agent is an anionic polymer, for purposes of the instant disclosure, it is considered as an anionic polymer of (d), notwithstanding it ability to independently act as a thickening agent. Therefore, the anionic polymers included below should be considered anionic polymers of (d).

Non-limiting examples of thickening agents include xanthan gum, guar gum, biosaccharide gum, cellulose, acacia Seneca gum, *sclerotium* gum, agarose, pectin, gellan gum, hyaluronic acid. In some instances, the one or more thickening agents may include polymeric thickening agents, for example, those selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/$C_{10}$-30 alkyl acrylate crosspolymer. In some instances, the thickening agent(s) are selected from carboxylic acid polymers (e.g., carbomer), crosslinked polyacrylate polymers, polyacrylamide polymers, polysaccharides, gums, and a combination thereof. Carbomer is a particularly useful and preferred thickening agent.

(i) Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerytritol. The carbomers are available as the Carbopol™ 900 series from B.F. Goodrich (e.g., Carbopol® 954). In addition, other suitable carboxylic acid polymeric agents include Ultrez® 10 (B.F. Goodrich) and copolymers of C10-30 alkyl acrylates with one or more monomers of acrylic acid, methacrylic acid, or one of their short chain (i.e., $C_{1-4}$ alcohol) esters, wherein the crosslinking agent is an allyl ether of sucrose or pentaerytritol. These copolymers are known as acrylates/$C_{10}$-C30 alkyl acrylate crosspolymers and are commercially available as Carbopol™ 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and combinations thereof.

(ii) Crosslinked Polyacrylate Polymers

The compositions of the present disclosure can optionally contain crosslinked polyacrylate polymers useful as thickeners or gelling agents including both cationic and nonionic polymers.

(iii) Polyacrylamide Polymers

The compositions of the present disclosure can optionally contain polyacrylamide polymers, especially polyacrylamide polymers including substituted branched or unbranched polymers. Among these polyacrylamide polymers is the polymer given the CTFA designation polyacrylamide and isoparaffin and laureth-7, available under the Tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The compositions may also contain thickening and texturising gels of the type as exemplified by the product range called Lubrajel® from United Guardian. These gels have moisturizing, viscosifying, stabilizing properties.

(iv) Polysaccharides

A wide variety of polysaccharides can be useful herein. "Polysaccharides" refer to gelling agents that contain a backbone of repeating sugar (i.e., carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and combinations thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™. CS11 from Michel Mercier Products Inc.

(v) Gums

Other thickening and gelling agents useful herein include materials which are primarily derived from natural sources. Non-limiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, biosaccharide gum, and combinations thereof.

Additional examples of water-soluble thickeners include water-soluble natural polymers, water-soluble synthetic polymers, clay minerals and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, furcellaran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic hetero-polysaccharide derived form callus of plants belonging to Polyantes sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

The total amount of thickening agent(s) that are not anionic polymers in the cleansing compositions, if present, may vary but are typically in an amount of from about 0.01 to about 10 wt. %, from based on the total weight of the cleansing composition. In some instances, the total amount of thickening agents in the cleansing compositions that are not anionic polymers is from about 0.01 to about 5 wt. %, from about 0.01 to about 3 wt. %, from about 0.05 to about 10 wt. %, from about 0.05 to about 5 wt. %, from about 0.05 to about 3 wt. %, from about 0.1 to about 10 wt. %, from about 0.1 to about 5 wt. %, or from about 0.1 to about 3 wt. %, based on the total weight of the cleansing composition.

Non-Silicone Fatty Compounds

The term "non-silicone fatty compound" means a fatty compound that does not contain any silicon atoms (Si). Non-limiting examples of non-silicone fatty compounds include oils, mineral oil, fatty alcohols, fatty acids, fatty alcohol derivatives, fatty acid derivatives, esters of fatty alcohols, hydroxy-substituted fatty acids, waxes, triglyceride compounds, lanolin, or a combination thereof. Non-limiting examples of the fatty alcohols, fatty acids, fatty alcohol derivatives, and fatty acid derivatives are found in International Cosmetic Ingredient Dictionary, Sixteenth Edition, 2016, which is incorporated by reference herein in its entirety.

Fatty alcohols useful herein include those having from about 10 to about 30 carbon atoms, from about 12 to about 22 carbon atoms, and from about 16 to about 22 carbon atoms. These fatty alcohols can be straight or branched chain alcohols and can be saturated or unsaturated. Nonlimiting examples of fatty alcohols include decyl alcohol, undecyl alcohol, dodecyl, myristyl, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol and a combination thereof. In some cases, the fatty alcohols are those selected from the group consisting of cetyl alcohol, stearyl alcohol, isostearyl alcohol, oleyl alcohol, and a combination thereof.

Fatty acids useful herein include those having from about 10 to about 30 carbon atoms, from about 12 to about 22 carbon atoms, and from about 16 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Nonlimiting examples of fatty acids include lauric acid, palmitic acid, stearic acid, behenic acid, arachidonic acid, oleic acid, isostearic acid, sebacic acid, and a combination thereof. In some cases, the fatty acids are selected from the group consisting of palmitic acid, stearic acid, and a combination thereof.

In some instance, the one or more non-silicone fatty compounds include one or more non-silicone oils. The term "oil" as used herein describes any material which is substantially insoluble in water and substantially liquid at room temperature (25° C.). The oils may be natural oil, synthetic oils, hydrocarbon-based oils, etc., but natural oils are often desired. Non-limiting examples of natural oils include oils from plants, animals, and mineral sources, for example, coconut oil, wheat germ oil, sunflower seed oil, avocado oil, jojoba oil, babassu oil, macadamia oil, almond oil, apricot kernel oil, carrot oil, castor oil, citrus seed oil, corn oil, cottonseed oil, jojoba oil, linseed oil, mineral oil, mink oil, olive oil, palm kernel oil, peach kernel oil, peanut oil, rapeseed oil, safflower oil, sesame oil, soybean oil, vegetable oil, wheat germ oil, and a combination thereof. In some cases, soybean oil may be particularly useful.

The total amount of non-silicone fatty compounds, if present, can vary but are typically in an amount of about 0.001 to about 10 wt. %, based on the total weight of the cleansing composition. In some cases, the total amount of non-silicone fatty compounds is about 0.005 to about 5 wt. %, about 0.005 to about 3 wt. %, about 0.01 to about 10 wt. %, about 0.01 to about 5 wt. %, about 0.01 to about 3 wt. %, or about 0.01 to about 1 wt. % of the one or more non-silicone fatty compounds, based on the total weight of the cleansing composition.

Viscosity

The viscosity of the cleansing compositions discussed throughout the instant disclosure will vary. Nonetheless, the cleansing composition typically has a viscosity similar to other cream/paste cleansing compositions, including facial cleansers, shampoo compositions, and few conditioning compositions. In certain embodiments, the viscosity of the cleansing composition is from about 50 Pa-s to about 5,000 Pa-s at 25° C., the shear rate of 1 $s^{-1}$ (second). In further embodiments, the viscosity if from about 50 Pa-s to about 4,000 Pa-s, about 50 Pa-s to about 3,000 Pa-s, about 50 Pa-s to about 2,000 Pa-s, about 50 Pa-s to about 1,000 Pa-s, about 50 Pa-s to about 500 Pa-s, about 75 Pa-s to about 5,000 Pa-s, 75 Pa-s to about 4,000 Pa-s, about 75 Pa-s to about 3,000 Pa-s, about 75 Pa-s to about 2,000 Pa-s, about 75 Pa-s to about 1,000 Pa-s, about 75 Pa-s to about 500 Pa-s, about 100 Pa-s to about 5,000 Pa-s, 100 Pa-s to about 4,000 Pa-s, about 100 Pa-s to about 3,000 Pa-s, about 100 Pa-s to about 2,000 Pa-s, about 100 Pa-s to about 1,000 Pa-s, or about 100 Pa-s to about 500 Pa-s at 25° C., the shear rate of 1 $s^{-1}$. Preferably, the viscosity if from about 50 Pa-s to about 500 Pa-s at 25° C., the shear rate of 1 $s^{-1}$. The viscosity can be measured with a DHR-2 Rheometer.

pH

The pH of the cleansing composition can vary. Nonetheless, in various embodiments, the pH of the cleansing composition is from about 4 to about 8. In certain instances, it is preferable for the pH to be acidic or slightly acidic, having a pH of less than 7. Accordingly, in further embodiments, the pH of the cleansing compositions from about 4 to about 7, about 4 to less than 7, about 4 to about 6.8, about 4 to about 6.6, about 5 to about 6.5, about 4.5 to about 7, about 4.5 to less than 7, about 4.5 to about 6.8, about 4.5 to about 6.6, about 4.5 to about 6.5, about 5 to about 7, about 5 to less than 7, about 5 to about 6.8, about 5 to about 6.6, or about 5 to about 6.5.

Preferred Embodiments

In certain embodiments of the instant disclosure, the cleansing compositions comprises, consists essentially of, or consists of:

(a) about 5 to about 25 wt. %, preferably about 5 to about 20 wt. %, more preferably about 10 to about 20 wt. % of one or more anionic surfactants selected from sulfate surfactants, acyl amino acid surfactants, alkyl sulfonates, acyl isethionates, alkyl sulfosuccinates, alkyl sulfoacetates, alkoxylated monoacids, salts thereof, or combinations thereof;

(b) about 1 to about 10 wt. % of one or more nonionic emulsifiers having a Hydrophile-Lipophile Balance (HLB) of about 6 or less selected from sorbitan esters, glyceryl esters, polyglyceryl esters, glycol esters, sucrose esters, methyl glucose esters, ethoxylated methyl glucose esters, or a combination thereof, preferably wherein at least one of the one or more emulsifiers having an HLB of about 6 or less is a glycol ester, preferably wherein the at least one glycol ester is selected from glycol distearate, glycol hydroxystearate, glycol oleate, glycol ricinoleate, glycol stearate, propylene glycol isostearate, propylene glycol hydroxystearate, propylene glycol laurate, propylene glycol myristate, propylene glycol oleate, propylene glycol ricinoleate, propylene glycol stearate, or combinations thereof;

(c) about 0.05 to about 5 wt. %, preferably about 0.1 to about 3 wt. %, more preferably about 0.1 to about 2 wt. % of one or more salts providing divalent cations having a charge density of about 40 to about 200 $C/mm^3$ and a water solubility of at least 400 g/L, wherein preferably the one or more salts providing divalent cations are selected from magnesium salts, calcium salts, or a combination thereof, even more preferably wherein the one or more salts are selected from magnesium chloride, calcium chloride, magnesium sulfate, magnesium thiosulfate, calcium sulfate, zinc sulfate, calcium thiosulfate, magnesium pyrrolidone carboxylate (magnesium pidolate), calcium pyrrolidone carboxylate (calcium pidolate), magnesium gluconate, or a combination thereof, preferably wherein the one or more salts providing divalent cations are selected from magnesium chloride, calcium chloride, magnesium sulfate, zinc sulfate, calcium sulfate, or a combination thereof;

(d) about 0.5 to about 6 wt. %, about 0.5 to about 4 wt. %, more preferably about 1 to about 3 wt. % of one or more anionic polymers, preferably wherein the one or more anionic polymers are selected from anionic polymers having carboxylate, sulfate, and/or sulfonate groups; more preferably wherein the one or more anionic polymers are selected from copolymer of two or more monomers selected from acrylic acid, methacrylic acid, vinyl monomers, and (meth)acrylamide, even more preferably wherein at least one of the one or more anionic polymers is acrylates copolymer;

(e) about 10 to about 55 wt. % of one or more water soluble solvents selected from glycerin, $C_2$-$C_6$ monoalcohols, polyols (polyhydric alcohols), glycols, and a combination thereof, preferably wherein at least one of the one or more water soluble solvents is selected from glycerin, glycols, or a combination thereof, even more preferably wherein at least one of the water soluble solvents is glycerin; and (f) about 15 to about 65 wt. %, preferably about 25 to about 55 wt. %, even more preferably about 30 to about 50 wt. % of water;

(g) optionally, about 0.01 to about 10 wt. %, preferably about 0.1 to about 8 wt. %, more preferably about 1 to about 5 wt. % of one or more miscellaneous ingredients, preferably wherein the one or more miscellaneous ingredients are selected from pH adjusters, salts, fragrances, preservatives, antioxidants, skin active agents, anti-wrinkle agent, UV filters, de-pigmenting agents, chelating agents, compositions colorants, fillers, humectants, emollients, botanical extracts, amino acids, peptides, proteins, or a combination thereof;

wherein all percentages by weight are based on a total weight of the composition; and the composition is free or essentially free from sulfate-based surfactants.

Preferably, the composition has a lamellar liquid crystal structure. Further, the composition preferably has a pH of about 4 to about 7, preferably about 5 to less than 7, more preferably about 5 to about 6.8. The cleansing composition is preferably free or essentially free of silicones. The weight ratio of (c) to (d) is preferably about 1:0.5 to about 1:3 (c):(d), preferably about 1:0.6 to about 1:2.5, more preferably about 1:0.8 to about 1:2. The weight ratio of (e) to (f) is about 0.5:1 to 2:1, preferably about 0.6:1 to about 1.5:1, more preferably about 0.7:1.8:1. Preferably, the viscosity if from about 50 Pa-s to about 500 Pa-s at 25° C., the shear rate of 1 $s^{-1}$.

In certain embodiments of the instant disclosure, the cleansing compositions comprises, consists essentially of, or consists of:

(a) about 5 to about 25 wt. %, preferably about 5 to about 20 wt. %, more preferably about 10 to about 20 wt. % of one or more sulfate surfactants selected from alkyl sulfates, alkyl ether sulfates, or a combination thereof, and/or one or more non-sulfate anionic surfactants, wherein the one or more non-sulfate surfactants are selected from acyl amino acid surfactants, alkyl sulfonates, acyl isethionates, alkyl sulfosuccinates, alkyl sulfoacetates, alkoxylated monoacids, salts thereof, or combinations thereof, wherein at least one of the one or more non-sulfate anionic surfactants is an acyl amino acid surfactant selected from acyl sarcosinates, acyl taurates, acyl glycinates, acyl glutamates, salts thereof, or a combination thereof, more preferably wherein at least one of the one or more acyl amino acid surfactants is an acyl glycinate, an acyl glutamate, or a combination thereof, wherein the acyl glycinates are selected from sodium cocoyl glycinate, sodium lauroyl glycinate, sodium myristoyl glycinate, potassium lauroyl glycinate, potassium cocoyl glycinate, or a combination thereof and the acyl glutamates are selected from acyl glutamate selected from dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, triethanolamine mono-cocoyl glutamate, triethanolamine lauroylglutamate, disodium cocoyl glutamate, or a combination thereof;

(b) about 1 to about 10 wt. % of one or more nonionic emulsifiers having a Hydrophile-Lipophile Balance (HLB) of about 6 or less selected from sorbitan esters, glyceryl esters, polyglyceryl esters, glycol esters, sucrose esters, methyl glucose esters, ethoxylated methyl glucose esters, or a combination thereof, preferably wherein at least one of the one or more emulsifiers having an HLB of about 6 or less is a glycol ester, preferably wherein the at least one glycol ester is selected from glycol distearate, glycol hydroxystearate, glycol oleate, glycol ricinoleate, glycol stearate, propylene glycol isostearate, propylene glycol hydroxystearate, propylene glycol laurate, propylene glycol myristate, propylene glycol oleate, propylene glycol ricinoleate, propylene glycol stearate, or combinations thereof;

(c) about 0.05 to about 5 wt. %, preferably about 0.1 to about 3 wt. %, more preferably about 0.1 to about 2 wt. % of one or more salts providing divalent cations having a charge density of about 40 to about 200 C/$mm^3$ and a water solubility of at least 400 g/L, wherein preferably the one or more salts providing divalent cations are selected from magnesium salts, calcium salts, or a combination thereof, even more preferably wherein the one or more salts are selected from magnesium chloride, calcium chloride, magnesium sulfate, magnesium thiosulfate, calcium sulfate, calcium thiosulfate, magnesium pyrrolidone carboxylate (magnesium pidolate), calcium pyrrolidone carboxylate (calcium pidolate), magnesium gluconate, or a combination thereof, preferably wherein the one or more salts providing divalent cations are selected from magnesium chloride, calcium chloride, magnesium sulfate, zinc sulfate, calcium sulfate, or a combination thereof;

(d) about 0.5 to about 6 wt. %, about 0.5 to about 4 wt. %, more preferably about 1 to about 3 wt. % of one or more anionic polymers, preferably wherein the one or more anionic polymers are selected from anionic polymers having carboxylate, sulfate, and/or sulfonate groups; more preferably wherein the one or more anionic polymers are selected from copolymer of two or more monomers selected from acrylic acid, methacrylic acid, vinyl monomers, and (meth)acrylamide, even more preferably wherein at least one of the one or more anionic polymers is acrylates copolymer;

(e) about 10 to about 55 wt. % of one or more water soluble solvents selected from glycerin, $C_2$-$C_6$ monoalcohols, polyols (polyhydric alcohols), glycols, and a combination thereof, preferably wherein at least one of the one or more water soluble solvents is selected from glycerin, glycols, or a combination thereof, even more preferably wherein at least one of the water soluble solvents is glycerin; and (f) about 15 to about 65 wt. %, preferably about 25 to about 55 wt. %, even more preferably about 30 to about 50 wt. % of water;

(g) optionally, about 0.01 to about 10 wt. %, preferably about 0.1 to about 8 wt. %, more preferably about 1 to about 5 wt. % of one or more miscellaneous ingredients, preferably wherein the one or more miscellaneous ingredients are selected from pH adjusters, salts, fragrances, preservatives, antioxidants, skin active agents, anti-wrinkle agent, UV filters, de-pigmenting agents, chelating agents, compositions colorants, fillers, humectants, emollients, botanical extracts, amino acids, peptides, proteins, or a combination thereof;

wherein all percentages by weight are based on a total weight of the composition; and the composition is free or essentially free from sulfate-based surfactants.

Preferably, the composition has a lamellar liquid crystal structure. Further, the composition preferably has a pH of about 4 to about 7, preferably about 5 to less than 7, more preferably about 5 to about 6.8. The cleansing composition is preferably free or essentially free of silicones. The cleansing composition is preferably free or essentially free of silicones. The weight ratio of (c) to (d) is preferably about 1:0.5 to about 1:3 (c):(d), preferably about 1:0.6 to about 1:2.5, more preferably about 1:0.8 to about 1:2. The weight ratio of (e) to (f) is about 0.5:1 to 2:1, preferably about 0.6:1 to about 1.5:1, more preferably about 0.7:1.8:1. Preferably, the viscosity if from about 50 Pa-s to about 500 Pa-s at 25° C., the shear rate of 1 $s^{-1}$.

In another embodiments of the instant disclosure, the cleansing compositions comprises, consists essentially of, or consists of:

(a) about 5 to about 25 wt. %, preferably about 5 to about 20 wt. %, more preferably about 10 to about 20 wt. % of one or more non-sulfate anionic surfactants selected from sulfate surfactants, non-sulfate surfactants, or a combination thereof,
  wherein the sulfate surfactants are selected from sodium lauryl sulfate (SLS), sodium dodecyl sulfate (SDS), sodium lauryl ether sulfate (SLES), or a combination thereof, and
  wherein the one or more non-sulfate surfactants are selected from acyl amino acid surfactants, alkyl sulfonates, acyl isethionates, alkyl sulfosuccinates, alkyl sulfoacetates, alkoxylated monoacids, salts thereof, or combinations thereof, wherein at least one of the one or more non-sulfate anionic surfactants is an alkyl sulfosuccinate selected from disodium oleamido MIPA sulfosuccinate, disodium oleamido MEA sulfosuccinate, disodium lauryl sulfosuccinate, disodium laureth sulfosuccinate, diammonium lauryl sulfosuccinate, diammonium laureth sulfosuccinate, dioctyl sodium sulfosuccinate, disodium oleamide MEA sulfosuccinate, sodium dialkyl sulfosuccinate, or a combination thereof;

(b) about 1 to about 10 wt. % of one or more nonionic emulsifiers having a Hydrophile-Lipophile Balance (HLB) of about 6 or less selected from sorbitan esters, glyceryl esters, polyglyceryl esters, glycol esters, sucrose esters, methyl glucose esters, ethoxylated methyl glucose esters, or a combination thereof, preferably wherein at least one of the one or more emulsifiers having an HLB of about 6 or less is a glycol ester, preferably wherein the at least one glycol ester is selected from glycol distearate, glycol hydroxystearate, glycol oleate, glycol ricinoleate, glycol stearate, propylene glycol isostearate, propylene glycol hydroxystearate, propylene glycol laurate, propylene glycol myristate, propylene glycol oleate, propylene glycol ricinoleate, propylene glycol stearate, or combinations thereof;

(c) about 0.05 to about 5 wt. %, preferably about 0.1 to about 3 wt. %, more preferably about 0.1 to about 2 wt. % of one or more salts providing divalent cations having a charge density of about 40 to about 200 C/$mm^3$ and a water solubility of at least 400 g/L, wherein preferably the one or more salts providing divalent cations are selected from magnesium salts, calcium salts, or a combination thereof, even more preferably wherein the one or more salts are selected from magnesium chloride, calcium chloride, magnesium sulfate, magnesium thiosulfate, calcium sulfate, calcium thiosulfate, magnesium pyrrolidone carboxylate (magnesium pidolate), calcium pyrrolidone carboxylate (calcium pidolate), magnesium gluconate, or a combination thereof, preferably wherein the one or more salts providing divalent cations are selected from magnesium chloride, calcium chloride, magnesium sulfate, zinc sulfate, calcium sulfate, or a combination thereof;

(d) about 0.5 to about 6 wt. %, about 0.5 to about 4 wt. %, more preferably about 1 to about 3 wt. % of one or more anionic polymers, preferably wherein the one or more anionic polymers are selected from anionic polymers having carboxylate, sulfate, and/or sulfonate groups; more preferably wherein the one or more anionic polymers are selected from copolymer of two or more monomers selected from acrylic acid, methacrylic acid, vinyl monomers, and (meth)acrylamide, even more preferably wherein at least one of the one or more anionic polymers is acrylates copolymer;

(e) about 10 to about 55 wt. % of one or more water soluble solvents selected from glycerin, $C_2$-$C_6$ monoalcohols, polyols (polyhydric alcohols), glycols, and a combination thereof, preferably wherein at least one of the one or more water soluble solvents is selected from glycerin, glycols, or a combination thereof, even more preferably wherein at least one of the water soluble solvents is glycerin; and (f) about 15 to about 65 wt. %, preferably about 25 to about 55 wt. %, even more preferably about 30 to about 50 wt. % of water;

(g) optionally, about 0.01 to about 10 wt. %, preferably about 0.1 to about 8 wt. %, more preferably about 1 to about 5 wt. % of one or more miscellaneous ingredients, preferably wherein the one or more miscellaneous ingredients are selected from pH adjusters, salts, fragrances, preservatives, antioxidants, skin active agents, anti-wrinkle agent, UV filters, de-pigmenting agents, chelating agents, compositions colorants, fillers, humectants, emollients, botanical extracts, amino acids, peptides, proteins, or a combination thereof;
  wherein all percentages by weight are based on a total weight of the composition; and
  the composition is free or essentially free from sulfate-based surfactants.

Preferably, the composition has a lamellar liquid crystal structure. Further, the composition preferably has a pH of about 4 to about 7, preferably about 5 to less than 7, more preferably about 5 to about 6.8. The cleansing composition is preferably free or essentially free of silicones. The cleansing composition is preferably free or essentially free of silicones. The weight ratio of (c) to (d) is preferably about 1:0.5 to about 1:3 (c):(d), preferably about 1:0.6 to about 1:2.5, more preferably about 1:0.8 to about 1:2. The weight ratio of (e) to (f) is about 0.5:1 to 2:1, preferably about 0.6:1 to about 1.5:1, more preferably about 0.7:1.8:1. Preferably, the viscosity if from about 50 Pa-s to about 500 Pa-s at 25° C., the shear rate of 1 $s^{-1}$.

Methods

The cleansing compositions of the instant disclosure are particularly useful for cleansing and hydrating/moisturizing hair and skin. Accordingly, the cleansing compositions are useful in methods for cleansing hair and skin, methods of conditioning hair and skin, and methods for imparting smoothness, moisturization, or hydration to the skin. The methods typically comprise application of the cleansing composition to the hair or skin. The cleansing compositions can be massed or spread throughout the hair or skin and subsequently rinsed from the hair or skin. In a preferred embodiment, the cleansing composition are useful as a skin cleanser, for example, a skin cleanser for the face, i.e., a facial cleanser.

Examples

Various changes can be made in the above-described compositions and methods without departing from the scope of the invention. Accordingly, it is intended that all disclosure contained in the above description and in the examples given below, shall be interpreted as illustrative and not in a limiting sense.

The terms “a,” “an,” and “the” are understood to encompass the plural as well as the singular.

Thus, the term “a mixture thereof” or “a combination thereof” also relates to “mixtures thereof” or “combinations thereof.” Throughout the disclosure, the term “a combination thereof” may be used following a list of elements as shown in the following example where letters A-F represent the elements: “one or more elements selected from the group Example 1

| | | INVENTIVE | | | | COMPARATIVE | | | |
|---|---|---|---|---|---|---|---|---|---|
| | | A | B | C | D | E | F | G | H |
| (a) Acyl Amino Acid Surfactant | SODIUM COCOYL GLYCINATE | 14.4 | 14.4 | | 14.4 | 14.4 | 14.4 | 14.4 | 14.4 |
| | SODIUM COCOYL GLUTAMATE | 0.4 | | | | | | | |
| | DISODIUM COCOYL GLUTAMATE | 1.6 | | | | | | | |
| Non-Acyl Amino Acid | DISODIUM LAURETH SULFOSUCCINATE | | | 14.4 | | | | | |
| Total Anionic Surfactants | | 16.4 | 14.4 | 14.4 | 14.4 | 14.4 | 14.4 | 14.4 | 14.4 |
| (b) Nonionic Emulsify (HLB ≤ 6) | GLYCOL DISTEARATE (HLB = 5 − 6) | 3 | 3 | 3 | 3 | | | 3 | 3 |
| Nonionic Emulsifier > 6 | BEHENYL ALCOHOL (HLB = 16) | | | | | 3 | | | |
| (c) Divalent Cation | MAGNESIUM CHLORIDE | 0.6 | 0.6 | 0.6 | | | | 0.6 | 0.6 |
| | MAGNESIUM GLUCONATE | 0.5 | | | | | | | |
| | CALCIUM CHLORIDE | | | | 0.1 | | | | |
| Monovalent Cation | ADDITIONAL $NaCl_2$ | | | | | | 0.6 | | |
| (d) Anionic Polymer | ACRYLATES COPOLYMER | 1.1 | 1.1 | 1.1 | 1.1 | 1.1 | 1.1 | | |
| Nonionic Polymer | HYDROXYPROPYL STARCH PHOSPHATE | | | | | | | 1.1 | |
| Carbopol | | | | | | | | | 1.1 |
| Ratio of (c):(d) | | 1:1 | 1:1.8 | 1:1.8 | 1:1.8 | 1:1.8 | 1:1.8 | 1:1.8 | 1:1.8 |
| (e) Water Soluble Solvent | GLYCERIN | 33 | 42 | 42 | 42 | 42 | 42 | 42 | 42 |
| (g) Miscellaneous[1] | | ≤5 | ≤5 | ≤5 | ≤5 | ≤5 | ≤5 | ≤5 | ≤5 |
| (f) WATER | | 42 | 36 | 36 | 36 | 36 | 36 | 36 | 36 |
| Ratio of (e):(f) | | 0.8:1 | 1.2:1 | 1.2:1 | 1.2:1 | 1.2:1 | 1.2:1 | 1.2:1 | 1.2:1 |
| pH | | 6.6 | 6.6 | 6.6 | 6.6 | 6.6 | 6.6 | 6.6 | 6.6 |
| Viscosity[2] at 25° C., shear rate 1 $s^{-1}$ | | 50-500 Pa-s | | | | <50 | <50 | <50 | <50 |

[1]For example, pH adjusters, salts, fragrances, preservatives, antioxidants, chelating agents, compositions colorants, fillers, humectants, emollients, skin-active agents such as hydroxyacetophenone, botanical extracts, etc. (e.g., trisodium ethylenediamine disuccinate, sodium benzoate, hydroxyacetophenone, phenoxyethanol, sodium chloride, etc.)

[2]Measured at 25° C. with a DHR-2 Rheometer.

The foregoing disclosure illustrates and describes embodiments of the invention. The disclosure shows and describes only the preferred embodiments but it is understood that the invention is useable in various other combinations, modifications, and environments and is capable of changes or modifications within the scope of the inventive concepts as expressed herein, commensurate with the above teachings and/or the skill or knowledge of the relevant art. The embodiments described herein above are further intended to explain best modes known by applicant and to enable others skilled in the art to utilize the disclosure. Accordingly, the description is not intended to limit the invention.

As used herein, the terms “comprising,” “having,” and “including” (or “comprise,” “have,” and “include”) are used in their open, non-limiting sense. The phrase “consisting essentially of” limits the scope of a claim to the specified materials or steps and those that do not materially affect the basic and novel characteristics of the claimed invention.

consisting of A, B, C, D, E, F, and a combination thereof.” The term, “a combination thereof” does not require that the combination include all of A, B, C, D, E, and F (although all of A, B, C, D, E, and F may be included). Rather, it indicates that a combination of any two or more of A, B, C, D, E, and F can be included. In other words, it is equivalent to the phrase “one or more elements selected from the group consisting of A, B, C, D, E, F, and a combination of any two or more of A, B, C, D, E, and F.”

Likewise, the term “a salt thereof” also relates to “salts thereof.” Thus, where the disclosure refers to “an element selected from the group consisting of A, B, C, D, E, F, a salt thereof, and a combination thereof,” it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

The term "plurality" means "more than one" or "two or more."

Other than in the operating examples, or where otherwise indicated, all numbers expressing quantities of ingredients and/or reaction conditions can be modified in all instances by the term "about," meaning within +/−5% of the indicated number.

Some of the various categories of ingredients identified for the cleansing compositions may overlap. In such cases where overlap may exist and the composition/product includes two overlapping ingredients (or more than two overlapping ingredients), an overlapping ingredient does not represent more than one component. For example, a fatty acid may be defined as both a "fatty compound" and separately as a "surfactant." If a particular claimed composition/product includes both a fatty compound and a surfactant, a single fatty acid in a composition can serve as only the fatty compound or as only the emulsifier (a single fatty is not considered to simultaneously qualify as both the fatty compound and the surfactant).

All percentages, parts, and ratios herein are based upon the total weight of the compositions of the present invention, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically 1, 2, 3, 4 and 5, as well as sub ranges such as 2-5, 3-5, 2-3, 2-4, 1-4, etc.

The term "surfactant" includes salts of the surfactant, to the extent they exist, even if not explicitly stated. In other words, whenever the disclosure refers to a surfactant (or surfactants), it is intended that salts of the surfactants are also encompassed to the extent such salts exist, even though the specification may not specifically refer to a salt (or may not refer to a salt in every instance throughout the disclosure), for example, by using language such as "a salt thereof" or "salts thereof." Sodium and potassium are common cations that form salts with surfactants. However, additional cations such as ammonium ions, or alkanolammonium ions such as monoethanolammonium or triethanolammonium ions, may also form salts of surfactants.

All components positively set forth in the instant disclosure can be negatively excluded. In other words, the cleansing compositions of the instant disclosure may be free or essentially free of any one or more of the components positively set forth in the instant disclosure.

The term "substantially free" or "essentially free" as used herein means the specific material may be present in small amounts that do not materially affect the basic and novel characteristics of the claimed invention. For instance, there may be less than 1% by weight of a specific material added to a composition, based on the total weight of the compositions (provided that an amount of less than 1% by weight does not materially affect the basic and novel characteristics of the claimed invention). Similarly, when a composition is essentially free from a particular element, the composition may include less than 1 wt. %, less than 0.5 wt. %, less than 0.1 wt. %, less than 0.05 wt. %, or less than 0.01 wt. %, or none of the specified material. Furthermore, all components that are positively set forth in the instant disclosure may be essentially excluded from the claims, e.g., a claimed composition may be "free," "essentially free" (or "substantially free") of one or more components that are positively set forth in the instant disclosure.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A cleansing composition comprising:

(a) about 5 to about 25 wt. % of one or more anionic surfactants;

(b) about 1 to about 10 wt. % of one or more nonionic emulsifiers having a Hydrophile-Lipophile Balance (HLB) of about 6 or less, wherein at least one of the one or more nonionic emulsifiers is a glycol ester;

(c) about 0.1 to about 3 wt. % of one or more salts providing a divalent cation selected from magnesium salts, calcium salts, or a combination thereof;

(d) about 0.2 to about 4 wt. % of one or more anionic polymers selected from copolymers of two or more monomers selected from acrylic acid, methacrylic acid, vinyl monomers, and (meth)acrylamide;

wherein (c) and (d) are in a weight ratio of about 1.5:1 to about 1:5 ((c):(d));

(e) about 25 to about 50 wt. % of one or more water soluble solvents selected from glycerin, $C_2$-$C_6$ monoalcohols, polyols, glycols, or combinations thereof;

(f) about 25 to about 50 wt. % of water;

(g) optionally, about 0.1 to about 10 wt. % of one or more miscellaneous ingredients;

wherein all percentages by weight are based on a total weight of the compositions;

the composition is essentially free from sulfate-based surfactants;

and the composition has a lamellar liquid crystal structure.

2. A method for cleansing skin comprising applying the cleansing composition of claim 1 to the skin, and rinsing the composition from the skin.

3. The composition of claim 1, wherein the one or more anionic surfactants are selected from acyl amino acid surfactants, alkyl sulfonates, acyl isethionates, alkyl sulfosuccinates, alkyl sulfoacetates, alkoxylated monoacids, and salts thereof.

4. The cleansing composition of claim 3, wherein the one or more anionic surfactants are selected from acyl sarcosinates, acyl taurates, acyl glycinates, acyl glutamates, and salts thereof.

5. The cleansing composition of claim 4, wherein the one or more anionic surfactants comprise sodium cocoyl glycinate, sodium lauroyl glycinate, sodium myristoyl glycinate, potassium lauroyl glycinate, potassium cocoyl glycinate, or a combination thereof.

6. The cleansing composition of claim 3, wherein the one or more anionic surfactant comprise one or more acyl amino acid surfactants selected from sodium cocoyl taurate, sodium methyl cocoyl taurate, and disodium cocoyl taurate.

7. The cleansing composition of claim 3 comprising one or more acyl glutamates, wherein the one or more acyl glutamates are selected from dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium lauroyl glutamate, sodium myristoyl glutamate, sodium olivoyl glutamate, sodium palmitoyl glutamate, sodium stearoyl glutamate, sodium undecylenoyl glutamate, triethanolamine mono-cocoyl glutamate, and triethanolamine lauroylglutamate.

8. The cleansing composition of claim 3, wherein the one or more anionic surfactants comprise one or more alkyl sulfonates.

9. The cleansing composition of claim 3, wherein the one or more anionic surfactants comprise one or more acyl isethionate surfactants selected from sodium isethionate, sodium cocoyl isethionate, sodium lauroyl methyl isethionate, and sodium cocoyl methyl isethionate.

10. The cleansing composition of claim 3, wherein the one or more anionic surfactants comprise one or more alkyl sulfosuccinates selected from disodium oleamido MIPA sulfosuccinate, disodium oleamido MEA sulfosuccinate, disodium lauryl sulfosuccinate, disodium laureth sulfosuccinate, diammonium lauryl sulfosuccinate, diammonium laureth sulfosuccinate, dioctyl sodium sulfosuccinate, disodium oleamide MEA sulfosuccinate, and sodium dialkyl sulfosuccinate.

11. The cleansing composition of claim 3, wherein the one or more anionic surfactants comprise one or more alkyl sulfoacetates selected from C4-C18 fatty alcohol sulfoacetates.

12. The cleansing composition of claim 1, wherein the one or more salts providing divalent cations are selected from magnesium chloride, calcium chloride, magnesium sulfate, magnesium thiosulfate, calcium sulfate, calcium thiosulfate, magnesium pyrrolidone carboxylate, calcium pyrrolidone carboxylate, and magnesium gluconate.

13. The cleansing composition of claim 1, wherein the one or more nonionic emulsifiers having an HLB of about 6 or less comprise the at least on glycol ester, and one or more emulsifiers selected from sorbitan esters, glyceryl esters, polyglyceryl esters, sucrose esters, methyl glucose esters, ethoxylated methyl glucose esters, or combinations thereof.

14. The cleansing composition of claim 1, wherein the glycol ester is selected from glycol distearate, glycol hydroxystearate, glycol oleate, glycol ricinoleate, glycol stearate, propylene glycol isostearate, propylene glycol hydroxystearate, propylene glycol laurate, propylene glycol myristate, propylene glycol oleate, propylene glycol ricinoleate, and propylene glycol stearate.

15. The cleansing composition of claim 1, wherein the one or more anionic polymers comprise acrylates copolymer.

16. The cleansing composition of claim 1, wherein the one or more water soluble solvents comprise glycerin.

* * * * *